US006541508B2

(12) United States Patent
Ekwuribe et al.

(10) Patent No.: US 6,541,508 B2
(45) Date of Patent: Apr. 1, 2003

(54) TAXANE PRODRUGS

(75) Inventors: Nnochiri N. Ekwuribe, Cary; Christopher H. Price, Chapel Hill, both of NC (US); Gary S. Bartley, Florence, SC (US)

(73) Assignee: Nobex Corporation, Durham, NC (US)

( * ) Notice: Subject to any disclaimer, the term of this patent is extended or adjusted under 35 U.S.C. 154(b) by 23 days.

(21) Appl. No.: 09/802,739

(22) Filed: Mar. 9, 2001

(65) Prior Publication Data

US 2002/0013484 A1 Jan. 31, 2002

Related U.S. Application Data

(63) Continuation-in-part of application No. 09/476,974, filed on Dec. 31, 1999, now Pat. No. 6,380,405.
(60) Provisional application No. 60/153,579, filed on Sep. 13, 1999.

(51) Int. Cl.[7] ...................... A61K 31/337; C07D 305/14
(52) U.S. Cl. ....................... 514/449; 549/510; 549/511; 528/421
(58) Field of Search .......................... 514/449; 549/510, 549/511; 528/421

(56) References Cited

U.S. PATENT DOCUMENTS

| 5,407,683 A | 4/1995 | Shively ........................ 424/439 |
| 5,422,364 A | 6/1995 | Nicolaou et al. ............ 514/449 |
| 5,439,686 A | 8/1995 | Desai et al. .................. 424/451 |
| 5,484,809 A | 1/1996 | Hostetler et al. ............ 514/449 |
| 5,560,933 A | 10/1996 | Soon-Shiong et al. ...... 424/489 |
| 5,608,087 A | 3/1997 | Nicolaou et al. ............ 549/510 |
| 5,614,549 A | 3/1997 | Greenwald et al. ......... 514/449 |
| 5,795,909 A | 8/1998 | Shashoua et al. ........... 514/449 |
| 5,817,840 A | 10/1998 | Nicolaou et al. ............ 549/510 |
| 5,824,701 A | 10/1998 | Greenwald et al. ......... 514/449 |
| 5,932,462 A | 8/1999 | Harris et al. ................. 435/188 |

FOREIGN PATENT DOCUMENTS

| EP | 0 895 784 A1 | 2/1999 | .......... A61K/47/48 |
| JP | 07082291 | 3/1995 | .......... C07H/15/252 |
| WO | WO 93/24476 | 12/1993 | .......... C07D/305/14 |
| WO | WO 94/20453 | 9/1994 | .......... C07C/229/34 |
| WO | WO 96/23794 | 8/1996 | .......... C07D/491/22 |
| WO | WO97/33552 | 9/1997 | |
| WO | WO 98/07713 | 2/1998 | .......... C07D/305/14 |
| WO | WO98/58927 | 12/1998 | |
| WO | WO 99/30727 A1 | 6/1999 | .......... A61K/38/00 |
| WO | WO 99/48536 A2 | 9/1999 | .......... A61K/47/48 |
| WO | WO 00/64486 A2 | 11/2000 | .......... A61K/47/48 |
| WO | WO 01/13957 A2 | 3/2001 | .......... A61K/47/48 |
| WO | WO 01/19406 A2 | 3/2001 | .......... A61K/47/48 |

OTHER PUBLICATIONS

Adams et al., "Taxol: A History of Pharmaceutical Development and Current Pharmaceutical Concerns," *J. Natl. Cancer Inst. Monographs*, 15: 141–147(1993).

S. G. Arbuck, "Taxol (Paclitaxel): Future Directions," *Annals of Oncology*,5(Suppl 6): S59–S62 (1994).
Beijnen et al., "Bioanalysis, Pharmacokinetics, and Pharmacodynamics of the Novel Anticancer Drug Paclitaxel (Taxol)," *Sem. in Oncology*, 21:5(Suppl 8 Oct.) 53–62 (1994).
Delgado et al., "The Uses and Properties of PEG–Linked Proteins," *Critical Review in Therapeutic Drug Carrier Systems*, 9:(3,4) 249–304 (1992).
Deutsch et al., "Synthesis of Congeners and Prodrugs. 3. Water–Soluble Prodrugs of Taxol with Potent Antitumor Activity," *J. Medicinal Chem.*, 32: 788–792 (1989).
Greenwald et al., "Drug Delivery Systems: Water Soluble Taxol 2'–(Poly(thylene)Glycol) Ester Prodrugs—Design and in Vivo Effectiveness," *J. Medicinal Chem.*, 39: 424–431 (1996).
Greenwald et al., "Highly Water Soluble Taxol Derivatives: 7–Polyethylene Glycol Carbamates and Carbonates," *J. Org. Chem.*, 60: 331–336 (1995).
S. B. Horwitz, "TAXOL (Paclitaxel): Mechanisms of Action,"*Annals of Oncology*, 5 (Suppl. 6): S3–S6 (1994).
David G. I. Kingston, "Taxol: the Chemistry and Strucure–Activity Relationships of a Novel Anticancer Agent," *TIBTECH*, 12: 222–227 (Jun. 1994).
David G. I. Kingston, "The Chemistry of Taxol," *Pharmac. Ther.*, 52: 1–33 (1991).
Kohler et al., "Paclitaxel (Taxol)," *Pharmacotherapy*, 14:1 3–34 (1994).
Harry J. Long, "Paclitaxel (Taxol): A Novel Anticancer Chemotherapeutic Drug," *Mayo Clinic Proc.*, 69: 341–345 (1994).
Parekh et al., "The Transport and Binding of Taxol," *Gen. Pharac.*, 29:2 167–172 (1997).
N. J. Preston, "Paclitaxel (Taxol)—A Guide to Administration," *European J. of Cancer Care*, 5: 147–152 (1996).
Rowinsky et al., "The Clinical Pharmacology and Use of Antimicrotubule Agents in Cancer Chemotherapeutics," *Pharmac. Ther.*, 52: 35–84 (1991).
Rowinsky et al., "Taxol: The First of the Taxanes, an Important New Clas of Antitumor Agents," *Seminars in Oncology*, 19:6 646–662 (Dec. 1992).
Rowinsky et al., "Taxol: Pharmacology, Metabolism and Clinical Implications," *Cancer Surveys*, 17: 283–304 (1993).
Straubinger et al., "Novel Taxol Formulations: Taxol–Containing Liposomes," *J. Nat. Cancer Inst. Monographs*, 15: 69–78 (1993).
Paul Workman, "Pharmacokinetics and Cancer: Successes, Failures and Future Prospects," *Cancer Surveys*, 17: 1–26 (1993).
International Search Report, PCT/US00/24523, Date of Mailing: Aug. 6, 2001.

*Primary Examiner*—Ba K. Trinh
(74) *Attorney, Agent, or Firm*—Myers Bigel Sibley & Sajovec, P.A.

(57) ABSTRACT

Taxane prodrugs comprise a taxane joined by a hydrolyzable bond to one or more oligomers that comprise a polyethylene glycol moiety. The oligomer preferably further comprises a salt-forming moiety.

28 Claims, 4 Drawing Sheets

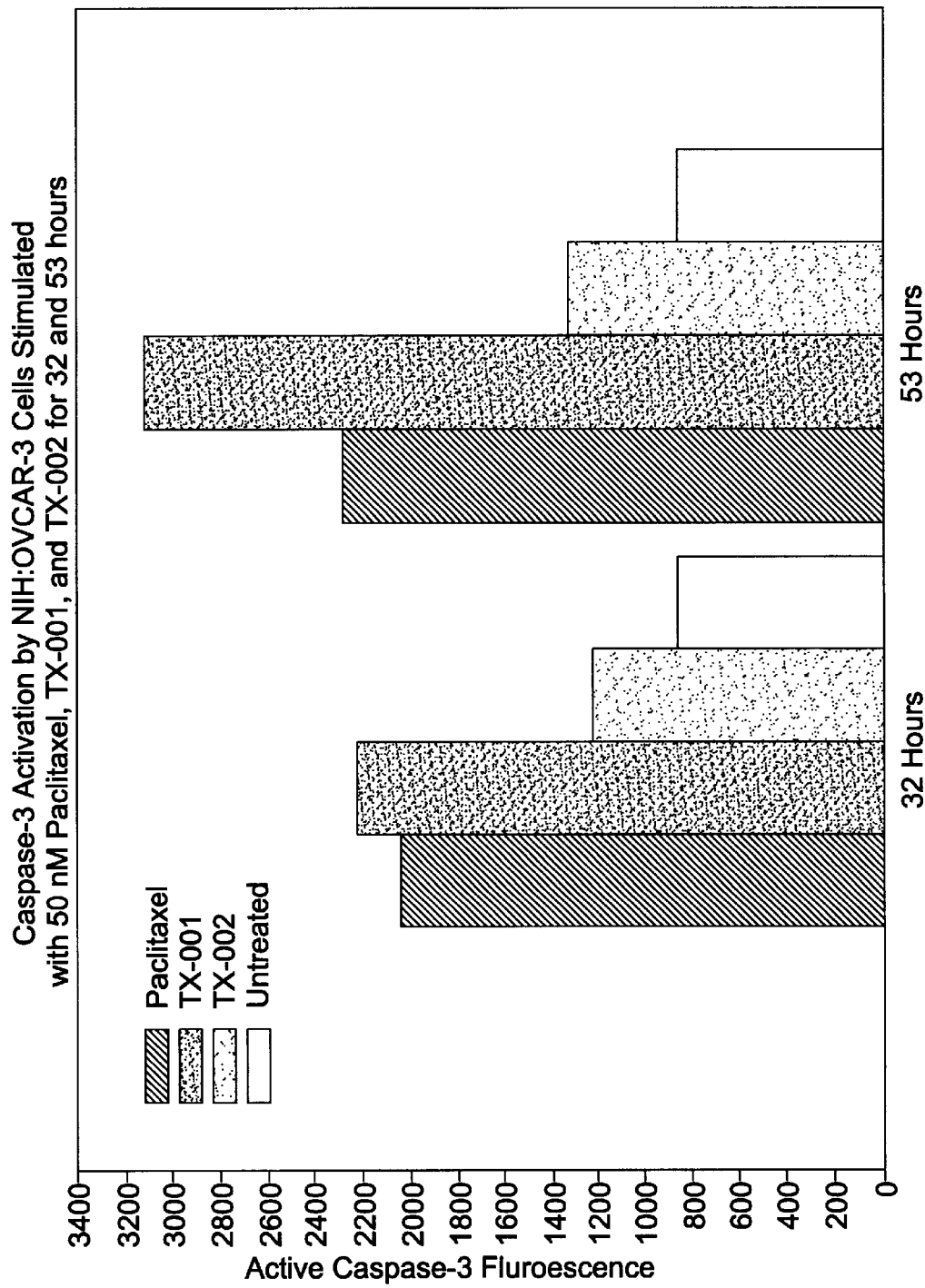

TAXANE PRODRUGS

RELATED APPLICATION

This application is a continuation-in-part of commonly owned, application Ser. No. 09/476,974 of Ekwuribe et al., filed Dec. 31, 1999, now U.S. Pat. No. 6,380,405 the disclosure of which is incorporated by reference herein in its entirety. The application also claims the priority benefit of provisional application 60/153,579 dated Sep. 13, 1999.

1. BACKGROUND OF THE INVENTION

1.1 Field of the Invention

The present invention relates generally to taxane-oligomer conjugates and to methods for making and using such conjugates. The taxane-oligomer conjugates of the invention operate as prodrugs, hydrolyzing under normal physiological conditions to provide therapeutically active taxanes, such as paclitaxel or docetaxel. The taxane-oligomer conjugates exhibit improved solubility characteristics, improved oral bioavailability, and an improved pharmacokinetic profile. The present invention also relates to pharmaceutical compositions comprising these taxane-oligomer conjugates and to methods of making and using such taxane-oligomer conjugates and pharmaceutical compositions.

1.2 Description of the Prior Art

Paclitaxel (Taxol) is a natural diterpene product isolated from the pacific yew tree (*Taxus brevifolia*). Wani et al. first isolated paclitaxel in 1971 by chemical and X-ray crystallographic methods. Paclitaxel is a complex diterpene having a taxane ring with a 4-membered oxetane ring and an ester side chain at position C-13. The complex structure of paclitaxel is as follows:

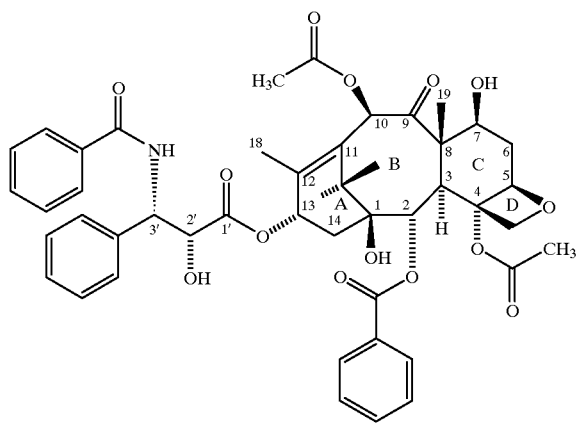

Paclitaxel has been approved for clinical use in the treatment of refractory ovarian cancer in the United States. (Markman 1991; McGuire et al. 1989). Paclitaxel has also been approved for treatment of breast cancer. (Holmes et al. 1991) Additionally, paclitaxel is a candidate for treatment of neoplasms of the skin (Einzig et al.) and head and neck carcinomas (Forastire et al. 1990). Paclitaxel is also useful for the treatment of polycystic kidney disease (Woo et al. 1994), lung cancer and malaria.

Paclitaxel mediates its anti-cancer effects by lowering the critical concentration of tubulin necessary for microtubule formation. Microtubules are polymers of tubulin in dynamic equilibrium with tubulin heterodimers that are composed of α and β protein subunits. Paclitaxel shifts the equilibrium towards microtubule assembly. Paclitaxel-induced microtubules are excessively stable, thereby inhibiting dynamic reorganization of the microtubule network, and resulting in microtubule bundles that form during all phases of the cell cycle and numerous abnormal mitotic asters that are not associated with centrioles.

Paclitaxel entered Phase I clinical trials in 1983, but immediately encountered formulation difficulties due to its aqueous insolubility. This difficulty was partially overcome by formulating Paclitaxel as an emulsion with Cremophor EL®. However, since paclitaxel must be given at relatively high dosages, large amounts of Cremophor EL® are required. When administered intravenously, such formulations can produce vasodilatation, labored breathing, lethargy, hypertension and death in dogs, and are also believed to be responsible for the allergic-type reactions observed during paclitaxel administration in humans. Accordingly, there is a need in the art for a means for administering paclitaxel which increases its water solubility and thereby avoids the need for formulating paclitaxel with potentially allergenic emulsion reagents.

Efforts to overcome the allergy problems of formulated paclitaxel have thus far been directed at lengthening the infusion time and premedicating patents with immunosuppressive agents, such as glucocorticoids and also with antihistamines. These agents have their own set of side effects and are an added cost to the already expensive cost of cancer treatment. Furthermore, while such agents have been shown to reduce the incidence and severity of hypersensitivity reactions, they are not fully protective. (Rowinsky et al. 1992). Accordingly, there is a need in the art for means for administering paclitaxel which avoids lengthened infusion times and the allergic reactions associated with emulsion reagents and thereby also avoids the need for such adjunctive treatment.

Several groups have investigated the synthesis of prodrug forms of paclitaxel. (Taylor 1994); (Kingston, D. G. 1991). Prodrugs are inactive or partially inactive chemical derivatives of drugs that are metabolized to yield the pharmacologically active drug. Studies have been directed toward synthesizing paclitaxel analogs where the 2' and/or 7-position is derivatized with groups that enhance water solubility. These efforts have yielded prodrug compounds that are more water-soluble than the parent compound while displaying the cytotoxic properties of paclitaxel upon activation. For example, increased water-solubility has been achieved by derivatizing paclitaxel with high molecular weight polyethylene glycol (PEG) polymers. (See Greenwald, et al. 1996; Greenwald et al. 1995). However, while these derivatized paclitaxel compounds have increased solubility, they also result in a corresponding decrease in drug load, due to the high molecular weight PEG necessary to achieve adequate solubility. Accordingly, there is a need in the art for taxane prodrugs which improve paclitaxel solubility without drastically increasing the molecular weight of the paclitaxel compound.

Efficient utilization of prodrugs, especially taxane prodrugs, requires that the properties of the prodrug must be adequately balanced to achieve a useful pharmacokinetic profile. In one aspect, it is desirable for the prodrug to be hydrophilic in order to enhance the ability to formulate the prodrug. On the other hand, the prodrug must be appropriately hydrophobic to permit interaction of the prodrug with biological membranes. There is therefore a need in the art for taxane prodrugs that accommodate the foregoing disparate requirements for useful therapeutic agents.

2. SUMMARY OF THE INVENTION

The present inventors have surprisingly and unexpectedly discovered taxane-oligomer compounds and salts of such compounds (collectively referred to herein as "taxane prodrugs") that significantly increase the water-solubility of taxane drugs without drastically increasing their molecular weight. The taxane prodrugs described herein eliminate the need for microemulsion formulation using Cremophor EL®.

Embodiments according to the present invention provide a taxane prodrug comprising a taxane joined by a hydrolyzable bond to an oligomer having the following formula:

(Formula 12)

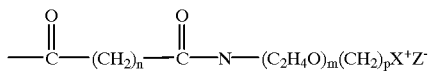

wherein n is from 1 to 12, m is from 1 to 25, p is from 2 to 12, $X^+$ is a positive ion and $Z^-$ is a negative ion.

In other embodiments of the present invention, the taxane is paclitaxel or a paclitaxel analog which retains some or all of the therapeutic activity of paclitaxel. Taxane may also be docetaxel.

The taxane prodrug may be derivatized by as many oligomers as there are sites on the taxane for attachment of such oligomers. For example, paclitaxel has 3 attachment sites (hydroxyl groups) and can therefore be derivatized by 1, 2 or 3 of the oligomers. Similarly, docetaxel paclitaxel has 4 attachment sites (hydroxyl groups) and can therefore be derivatized by 1, 2, 3 or 4 of the oligomers.

In another aspect, the taxane prodrugs can be delivered via oral administration to provide a therapeutically effective dose of the taxane to the bloodstream. Furthermore, the orally delivered prodrugs can provide a therapeutically effective dose of the taxane to the target organ or tissue.

Embodiments of the present invention also provide pharmaceutical compositions comprising the taxane prodrugs of the invention in association with a pharmaceutically acceptable carrier. Such pharmaceutical compositions may be formulated so as to be suitable for oral administration, and may be in a dosage form selected from the group consisting of: tablets, capsules, caplets, gelcaps, pills, liquid solutions, suspensions or elixirs, powders, lozenges, micronized particles and osmotic delivery systems. Methods for treating a mammalian subject having a paclitaxel-responsive disease condition are also provided. The mammalian subject is preferably a human.

In one aspect of the methods of treatment, the taxane prodrug is delivered via an oral route of administration to provide a therapeutically effective dose of the taxane into the bloodstream. In another aspect, the taxane prodrug is delivered via a parenteral route of administration, providing a therapeutically effective dose of the taxane to target organs and/or tissues. In yet another aspect, the taxane prodrug is delivered via an oral route of administration, providing a therapeutically effective dose of the taxane to target organs and/or tissues. Furthermore, the taxane prodrug may be administered in association with a pharmaceutically acceptable carrier.

In a further aspect, the taxane-responsive disease condition treated according to the therapeutic methods of the invention is selected from the group consisting of benign and malignant neoplasms, and may include hepatocellular carcinoma, urogenital carcinoma, liver metastases, gastrointestinal cancers, lymphoma, leukemia, melanoma, Kaposi's sarcoma, and cancers of the pancreas, kidney, cervix, breast, ovary, brain, and prostate. In one aspect, the disease condition comprises ovarian cancer and the taxane prodrug is administered optionally with cisplatin, either simultaneously or sequentially. In another aspect, the disease condition comprises breast cancer and the taxane prodrug is administered optionally with doxorubicin, either simultaneously or sequentially.

2.1 Definitions

As used herein the term "PEG" refers to straight or branched polyethylene glycol oligomer and monomers and also includes polyethylene glycol oligomers that have been modified to include groups which do not eliminate the amphiphilic properties of such oligomer, e.g. without limitation, alkyl, lower alkyl, aryl, amino-alkyl and amino-aryl. The term "PEG subunit" refers to a single polyethylene glycol unit, i.e., —$(CH_2CH_2O)$—.

As used herein, the term "lower alkyl" refers to a straight or branched chain hydrocarbon having from one to 8 carbon atoms.

As used herein, terms such as "non-hydrolyzable" and phrases such as "not hydrolyzable" are used to refer to bonds which cannot be hydrolyzed under normal physiological conditions, as well as bonds which are not rapidly hydrolyzed under normal physiological conditions such as carbamate and amide bonds. The term "hydrolyzable" refers to bonds which are hydrolyzed under physiological conditions. In a preferred aspect of the invention, 50% of the taxane prodrug is hydrolyzed in a normal population within 4 hours after intravenous administration.

A "therapeutically effective amount" is an amount necessary to prevent, delay or reduce the severity of the onset of disease, or an amount necessary to arrest or reduce the severity of an ongoing disease, and also includes an amount necessary to enhance normal physiological functioning.

As used herein, a "pharmaceutically acceptable" component (such as a salt, carrier, excipient or diluent) of a formulation according to the present invention is a component which (1) is compatible with the other ingredients of the formulation in that it can be combined with the taxane prodrugs of the present invention without eliminating the biological activity of the taxane prodrugs; and (2) is suitable for use with an animal (e.g., a human) without undue adverse side effects, such as toxicity, irritation, and allergic response. Side effects are "undue" when their risk outweighs the benefit provided by the pharmaceutical composition. Examples of pharmaceutically acceptable components include, without limitation, standard pharmaceutical carriers, such as phosphate buffered saline solutions, water, emulsions such as oil/water emulsions, microemulsions, and various types of wetting agents.

As used herein, the term "taxane" is used to refer to a class of compounds having a basic three ring structure which includes rings A, B and C of paclitaxel:

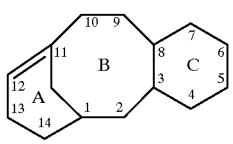

including, without limitation, paclitaxel and paclitaxel analogs which retain some or all of the anti-cancer activity of paclitaxel.

3. BRIEF DESCRIPTION OF THE DRAWINGS

FIG. 1 shows the conversion of acetate (Compound 4) (see Examples below) to paclitaxel over the course of 26 days at room temperature, where the acetate (Compound 4) was dissolved in wet acetonitrile. FIG. 1 shows that acetate (Compound 4) smoothly converted quantitatively into paclitaxel with no significant side product formation, as observed by analytical HPLC analysis.

FIG. 4 shows caspase-3 activation by NIH:OVCAR-3 cells stimulated with compounds of the present invention in comparison with paclitaxel.

4. DETAILED DESCRIPTION OF THE INVENTION

Figure 1:
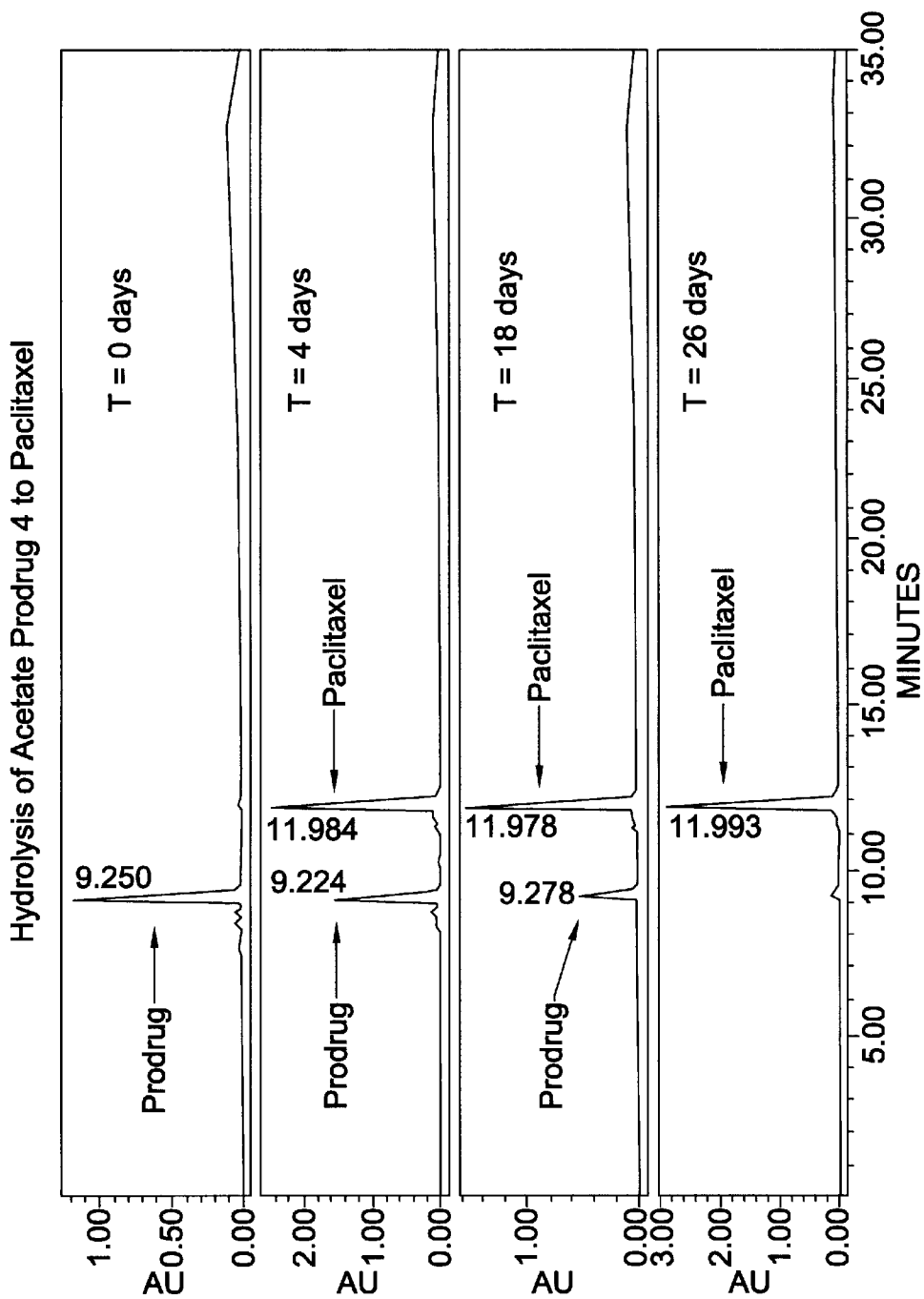

The ensuing detailed description is divided into sections for ease of reference only. Subject headings are not intended to limit the scope of the invention.

4.1 Taxane-Oligomer Prodrugs

The present invention provides taxane-oligomer prodrugs (also referred to herein as "taxane prodrugs"). The taxane prodrugs of the present invention generally comprise a taxane component and an oligomer component. The taxane prodrugs are generally useful in facilitating the formulation of taxanes in a hydrophilic formulation, the oral delivery of taxanes, and the delivery of taxanes to target organs and tissues.

4.1.1 Taxanes

Preferred taxanes are those having the constituents known in the art to be required for enhancement of microtubule formation, e.g., paclitaxel and docetaxel. The structures of paclitaxel and docetaxel are known in the art; however, for ease of reference, the structural formula of paclitaxel is set forth in Figure in Section 1.2 above, and the structural formula for docetaxel is as follows:

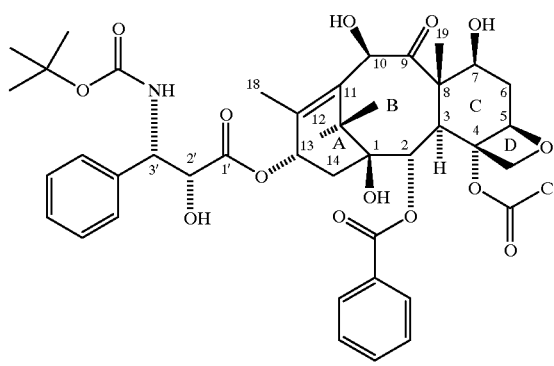

In a preferred mode, the taxane of the taxane prodrug is a paclitaxel analog. Many analogs of paclitaxel are known in the art which display more or less anti-cancer activity than paclitaxel itself. The present invention contemplates the use of any paclitaxel analog that does not have completely diminished anti-cancer activity.

In one class of analogs, the side chain N-benzoyl group is replaced with other acyl groups. One such analog, docetaxel (Taxotere®), has an N-t-butoxycarbonyl group in place of the N-benzoyl group of paclitaxel and also lacks the 10-acetate group. Docetaxel is known to be about five times as active as paclitaxel against paclitaxel-resistant cells and is currently in clinical use in both France and the U.S.A.

It is also known that reduction of the C-9 carbonyl group to an α-OH group causes a slight increase in tubulin-assembly activity. Additionally, it is known that a rearrangement product with a cyclopropane ring bridging the seven and eight-position is almost as cytotoxic as paclitaxel.

Further suitable taxanes for use in the taxane prodrugs of the present invention are paclitaxel derivatives having structural variations along the "northern perimeter" portion of the paclitaxel molecule. The "northern perimeter" comprises carbons 6–12, with oxygen functions at C-7, C-9 and C-10. Many such derivatives are known in the art, and it is known that such derivatives exhibit biological activity that is comparable to the bioactivity of paclitaxel. Thus, for example, it is known acylation of the C-7 hydroxyl group, or its replacement with hydrogen, does not significantly reduce the activity of paclitaxel. Additionally, replacement of the 10-acetoxy group with hydrogen causes only a small reduction in activity.

It has been noted that m-substituted benzoyl derivatives are more active than their p-substituted analogs, and are often more active than paclitaxel itself.

Another paclitaxel analog suitable for use in the taxane prodrugs of the present invention is A-nor-paclitaxel. This analog has tubulin-assembly activity that is only three times less than that of paclitaxel. A-nor-paclitaxel and paclitaxel have very similar molecular shapes, which may explain their similar tubulin-assembly activities.

4.1.2 Polymers/Oligomers

The PEG polymers/oligomers of the taxane prodrugs of the present invention may be straight or branched. Preferred oligomers have from 2 to 25 PEG units, more preferably from 2 to 20 PEG units, still more preferably from 2 to 15 PEG units. Ideally, the oligomer has from 2 to 10 PEG units, i.e., 2, 3, 4, 5, 6, 7, 8, 9 or 10 PEG units. In another aspect, the oligomer has a molecular weight which is not greater than 1000.

In a preferred mode, the PEG polymers/oligomers have the formula:

—(CH$_2$CH$_2$O)$_x$—CH$_3$ (Formula 1)

wherein X=2–25.

In a more preferred mode, X is from 2–20, still more preferably from 2–15, and most preferably from 2–10. Ideally, X is 2, 3, 4, 5, 6, 7, 8, 9 or 10.

Preferred oligomers are selected from the group consisting of:

(Formula 2)

wherein n is from 1 to 7, m is from 2 to 25, and R is a lower alkyl preferably selected from the group consisting of hydrogen, methyl, ethyl, propyl, isopropyl and t-butyl;

(Formula 3)

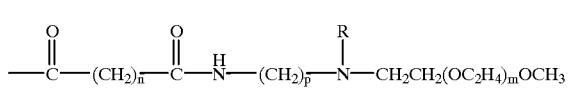

wherein n is from 1 to 6, p is from 2 to 8, m is from 2 to 25, and R is a lower alkyl, preferably selected from the group consisting of hydrogen, methyl, ethyl, propyl, isopropyl and t-butyl;

(Formula 4)

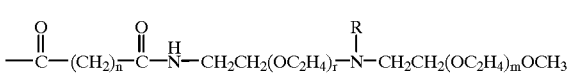

wherein n is from 1 to 6, m and r are each independently from 2 to 25, and R is a lower alkyl, preferably selected from the group consisting of hydrogen, methyl, ethyl, propyl, isopropyl and t-butyl;

(Formula 5)

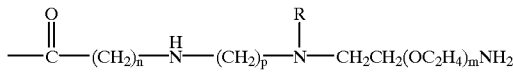

wherein n is from 1 to 6, p is from 2 to 8 and m is from 2 to 25 and R is a lower alkyl, preferably selected from the group consisting of hydrogen, methyl, ethyl, propyl, isopropyl and t-butyl;

(Formula 6)

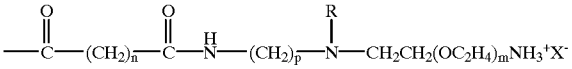

wherein n is from 1 to 6, p is from 2 to 8, m is from 2 to 25, $X^-$ is a negative ion, preferably selected from the group consisting of chloro, bromo, iodo, phosphate, acetate, carbonate, sulfate, tosylate and mesylate, and R is a lower alkyl, preferably selected from the group consisting of hydrogen, methyl, ethyl, propyl, isopropyl and t-butyl;

(Formula 7)

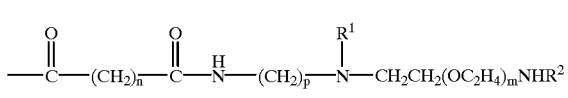

wherein n is from 1 to 6, p is from 2 to 8, m is from 2 to 25, and $R^1$ and $R^2$ are each independently a lower alkyl, preferably selected from the group consisting of methyl, ethyl, propyl, isopropyl, and t-butyl;

(Formula 8)

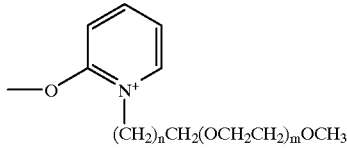

wherein n is from 1 to 6, p is from 2 to 8 and m is from 2 to 25;

(Formula 9)

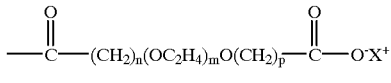

wherein n and p are each independently from 1 to 6, m is from 2 to 25 and $X^+$ is a positive ion, preferably selected from the group consisting of hydrogen, sodium, potassium, calcium, lithium and ammonium salts;

(Formula 10)

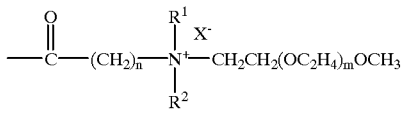

wherein n is from 1 to 5, m is from 2 to 25, $X^-$ is a negative ion, preferably selected from the group consisting of: chloro, bromo, iodo, phosphate, acetate, carbonate, sulfate and mesylate, and wherein $R^1$ and $R^2$ are each independently lower alkyl and are preferably independently selected from the group consisting of hydrogen, methyl, ethyl propyl, isopropyl and t-butyl;

(Formula 11)

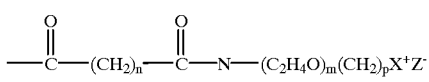

wherein n is from 1 to 6, m is from 2 to 25 and $X^+$ is a negative ion, preferably selected from the group consisting of: chloro, bromo, iodo, phosphate, acetate, carbonate, sulfate, and mesylate; and (Formula 12)

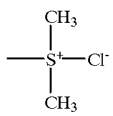

wherein n is from 1 to 12, m is from 1 to 25, p is from 2 to 12, $X^+$ is a positive ion and $Z^-$ is a negative ion. Preferably, n is from 2 to 8, and more preferably n is from 2 to 4. Preferably, p is from 2 to 8, and, more preferably, p is from 2 to 4. $X^+$ is preferably selected from the group consisting of $NH_3^+$ and trisubstituted sulfur, namely sulfur substituted with one or more R' and R" where R' and R" each is methyl, ethyl, propyl and butyl. For example $X^+Z^-$ is $$-S^+(CH_3)_2\ Cl^-$$

$Z^-$ is preferably selected from the group consisting of chloro anion, bromo anion, iodo anion, phosphate anion, acetate anion, trifluoracetate anion, carbonate anion, sulfate anion, and mesylate anion.

In any of the foregoing Formulae 1–12, the total number of PEG units is preferably from 2 to 25, more preferably from 2–20, still more preferably from 2–15, most preferably from 2–10. Ideally, the total number of PEG units is 2, 3, 4, 5, 6, 7, 8, 9 or 10. In formulae, such as Formula 4, which contain two PEG polymer segments, the preferred number of PEG units set forth in this paragraph may be contained completely in either of the two PEG polymer segments or may be distributed between the two PEG polymer segments.

The oligomer/polymer may also comprise one or more salt forming moieties. Preferred salt forming moieties are ammonium and carboxylate. Suitable salts also include any pharmaceutically acceptable acid-addition salts for oligomers/polymers having a basic amino group and pharmaceutically acceptable salts derived from pharmaceutically acceptable bases for oligomers/polymers having, e.g., a free carboxy group. Pharmaceutically acceptable salts of the acid may be prepared by treating the free acid with an appropriate base. Pharmaceutically acceptable base salts include, for example, alkali metal salts such as sodium or potassium, alkaline earth metal salts such as sodium or potassium, alkaline earth metal salts such as calcium or magnesium, and ammonium or alkyl ammonium salts.

4.2 Methods for Producing the Paclitaxel-PEG Conjugates

Paclitaxel is commercially available and can be isolated by methods known in the art from the bark of *Taxus brevifolia*. Paclitaxel can also be isolated from the leaves (or needles) of various Taxus species in yields comparable to the yield from *Taxus brevifolia* bark. U.S. Pat. No. 5,019,504 describes tissue-culture methods for producing paclitaxel. It is also known that paclitaxel is produced by the fungus *Taxomyces andreanae*.

Additionally, paclitaxel can be prepared by known synthetic methods, for example, as reported by Holton et al., *J. Am. Chem. Soc.* 116:1597–1598 (1994); Holton et al., *J. Am. Chem. Soc.* 116:1599–1600 (1994); and Nicolaou et al., *Nature* 367:630–634 (1994).

In the ensuing examples, the n, p, m, R, and $R^1$ and $R^2$ symbols are as described above in general Formulae 1–12.

4.2.1 Formula 1

The polymers of Formula 1 are commercially available and/or are readily synthesized by one of skill in the art without undue experimentation.

4.2.2 Formula 2

In the synthesis of the oligomers of Formula 2:

(Formula 2)

wherein n is from 1 to 7, m is from 2 to 25, and R is a lower alkyl, it is desirable to start with an ester of a fatty acid having a terminal carbon which bears a primary amino moiety. Such compounds are commercially available. The amino ester in an inert solvent is treated with a solution of monomethoxy polyethylene glycol of appropriate molecular weight bearing an aldehyde terminal carbon, followed by the addition of a solution of sodium borohydride. The product is purified after solvent extraction by column chromatography.

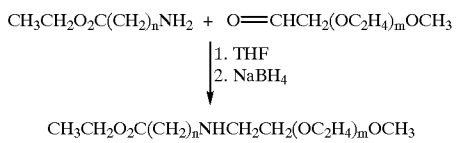

wherein n and m are as previously defined.

Sometimes it is desirable to alkylate the secondary amine moiety to form a desired oligomer bearing a tertiary amine. A solution of the oligomer in an inert solvent is treated with one equivalent of alkyl halide. The product is purified after solvent extraction by column chromatography.

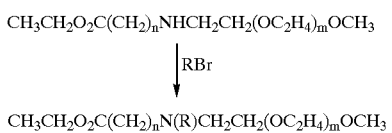

The ester is converted to an acid by treating it in an inert solvent with a dilute solution of sodium hydroxide at room temperature. The free acid is purified after solvent extraction by column chromatography. The acid is coupled to the drug after in situ activation.

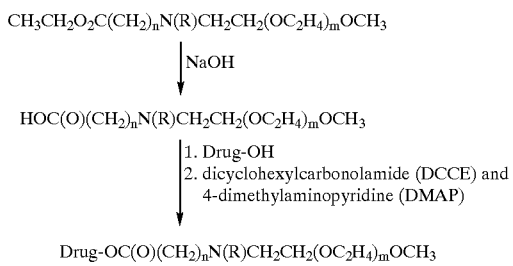

The drug in these examples can be, for example, paclitaxel or docetaxel.

It is sometimes desirable to synthesize the drug-oligomer by starting with the therapeutic compound derivatized as an ester of fatty acid having a terminal carbon which bears a halide and an appropriate monomethoxy-polyethylene glycol with a terminal carbon bearing a primary amino moiety. The polyethylene glycol reagent is dissolved in an inert solvent at room temperature. An equivalent amount of the drug-halide is dissolved in an inert solvent and added slowly to the solution of polyethylene glycol. The product is purified after solvent extraction using column chromatography.

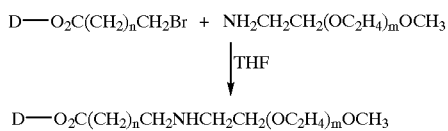

The ester is hydrolyzed with a dilute solution of sodium hydroxide as in the previous procedure and coupled to the drug (e.g., paclitaxel or docetaxel) after in situ activation as in the previous example.

4.2.3 Formula 3

In the synthesis of the oligomer of Formula 3:

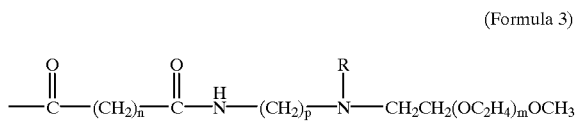
(Formula 3)

wherein n is from 1 to 6, p is from 2 to 8, m is from 2 to 25, and R is a lower alkyl, it is desirable to start with a half-ester of a dicarboxylic acid of an aliphatic compound and an amino-containing polyethylene. In the synthesis of the amino-containing polyethylene, an appropriate molecular weight monomethyl polyethylene glycol having an aldehyde moiety at the terminal end is treated in an inert solvent with an aliphatic compound bearing amino moieties at the two terminal carbons. One amino moiety is protected with tert-butoxycarbonyl while the free amine reacts with the aldehyde moiety. The product is purified after solvent extraction column chromatography. The product is deprotected by treating in an inert solvent with trifluoroacetic acid, neutralizing the acid and purifying after solvent extraction using column chromatography.

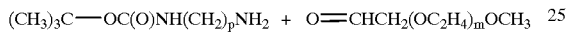
(CH$_3$)$_3$C—OC(O)NH(CH$_2$)$_p$NH$_2$ + O=CHCH$_2$(OC$_2$H$_4$)$_m$OCH$_3$

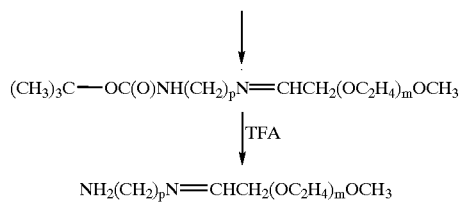
(CH$_3$)$_3$C—OC(O)NH(CH$_2$)$_p$N=CHCH$_2$(OC$_2$H$_4$)$_m$OCH$_3$

|TFA

NH$_2$(CH$_2$)$_p$N=CHCH$_2$(OC$_2$H$_4$)$_m$OCH$_3$

The half ester in an inert solvent is treated with a solution of the amino-derivatized polyethylene glycol at room temperature after an in situ activation of the acid. The product is purified by column chromatography after solvent extraction. The imino moiety is reduced by treating with a solution of sodium borohydride and purified as in the previous procedure.

It is sometimes desirable to alkylate the secondary amine. To achieve this end, the oligomer is dissolved in an inert solvent and treated with a solution of an alkyl halide in an inert solvent.

The ester is hydrolyzed, activated in situ, and coupled to the therapeutic compound (e.g., paclitaxel or docetaxel).

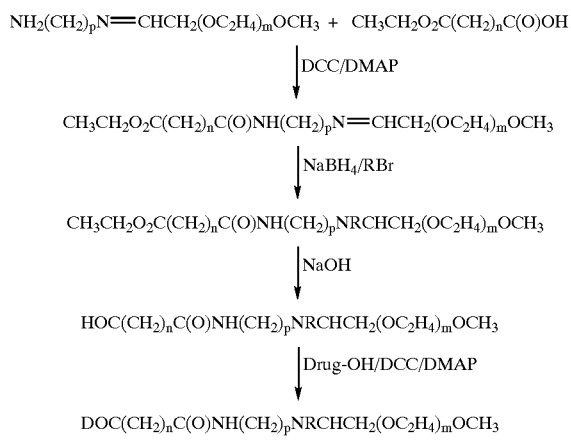
NH$_2$(CH$_2$)$_p$N=CHCH$_2$(OC$_2$H$_4$)$_m$OCH$_3$ + CH$_3$CH$_2$O$_2$C(CH$_2$)$_n$C(O)OH

|DCC/DMAP

CH$_3$CH$_2$O$_2$C(CH$_2$)$_n$C(O)NH(CH$_2$)$_p$N=CHCH$_2$(OC$_2$H$_4$)$_m$OCH$_3$

|NaBH$_4$/RBr

CH$_3$CH$_2$O$_2$C(CH$_2$)$_n$C(O)NH(CH$_2$)$_p$NRCHCH$_2$(OC$_2$H$_4$)$_m$OCH$_3$

|NaOH

HOC(CH$_2$)$_n$C(O)NH(CH$_2$)$_p$NRCHCH$_2$(OC$_2$H$_4$)$_m$OCH$_3$

|Drug-OH/DCC/DMAP

DOC(CH$_2$)$_n$C(O)NH(CH$_2$)$_p$NRCHCH$_2$(OC$_2$H$_4$)$_m$OCH$_3$ where D indicates the drug component of the drug-amphiphile conjugate. The amphiphilic drug conjugate is converted to a salt form to improve aqueous solubility as necessary using a pharmaceutically acceptable acid.

4.2.4 Formula 4

The procedure for the synthesis of the oligomer of Formula 4:

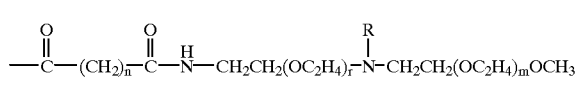
(Formula 4)

wherein n is from 1 to 6, m and r are each independently from 2 to 25, and R is a lower alkyl, is the same as for the oligomer of Formula 3 with the exception that the aliphatic diamino moieties are replaced with polyethylene glycol diamine.

4.2.5 Formula 5

In the synthesis of a prodrug comprising the oligomer of Formula 5:

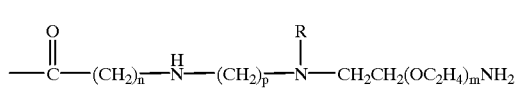
(Formula 5)

wherein n is from 1 to 6, p is from 2 to 8 and m is from 2 to 25 and R is a lower alkyl, the drug bearing a hydroxyl moiety is treated in an inert solvent with an aliphatic acid anhydride to form a half ester. The half-ester is dissolved in an inert solvent, activated and treated with one equivalent of a polyethylene glycol of appropriate molecular weight, in which the terminal hydroxyl moieties are replaced with amino moieties.

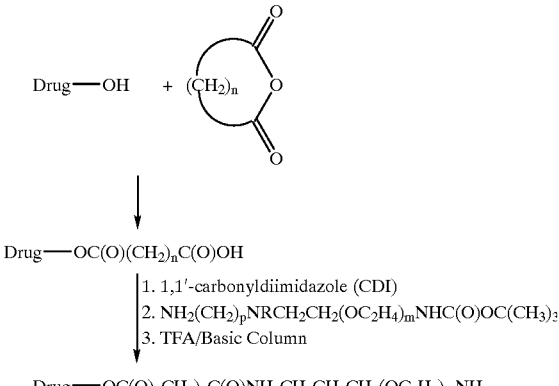
Drug—OH + (CH$_2$)$_n$

Drug—OC(O)(CH$_2$)$_n$C(O)OH

|1. 1,1'-carbonyldiimidazole (CDI)
|2. NH$_2$(CH$_2$)$_p$NRCH$_2$CH$_2$(OC$_2$H$_4$)$_m$NHC(O)OC(CH$_3$)$_3$
|3. TFA/Basic Column Drug—OC(O)$_9$CH$_2$)$_n$C(O)NH$_2$CH$_2$CH$_2$CH$_2$(OC$_2$H$_4$)$_m$NH$_2$ where all substituent groups (e.g., n, m and p) are as previously defined.

4.2.6 Formula 6

The oligomer of Formula 6:

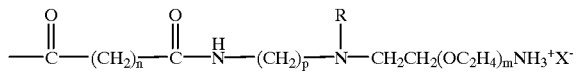
(Formula 6)

wherein n is from 1 to 6, p is from 2 to 8, m is from 2 to 25, $X^-$ is a negative ion, is prepared by treating the compound represented by Formula 5 with a pharmaceutically acceptable acid to obtain the appropriate salt. The salt increases the water-solubility of the amphiphilic drug conjugate.

4.2.7 Formula 7

The synthesis of the oligomer of Formula 7:

(Formula 7)

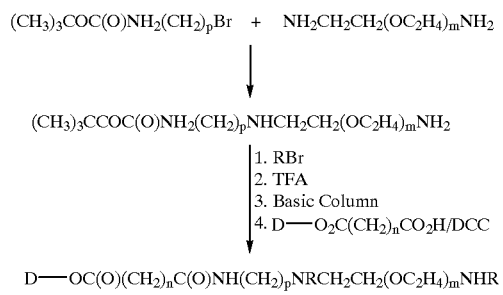

wherein n is from 1 to 6, p is from 2 to 8, m is from 2 to 25, and $R^1$ and $R^2$ are each independently a lower alkyl, is analogous to the synthesis of the oligomer of Formula 5, with the exception that the end-terminal amino moiety is alkylated with the halide of a short chain alkyl group such as methyl, ethyl, propyl, isopropyl or t-butyl before reacting to the half-ester of the drug.

$(CH_3)_3COC(O)NH_2(CH_2)_pBr + NH_2CH_2CH_2(OC_2H_4)_mNH_2$

↓

$(CH_3)_3CCOC(O)NH_2(CH_2)_pNHCH_2CH_2(OC_2H_4)_mNH_2$

1. RBr
2. TFA
3. Basic Column
4. $D—O_2C(CH_2)_nCO_2H/DCC$ $D—OC(O)(CH_2)_nC(O)NH(CH_2)_pNRCH_2CH_2(OC_2H_4)_mNHR$ where n, m and R are as previously defined.

4.2.8 Formula 8

In the synthesis of the oligomer of Formula 8:

(Formula 8)

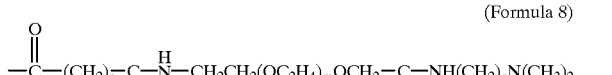

wherein n is from 1 to 6, p is from 2 to 8 and m is from 2 to 25, the half-ester of the aliphatic dicarboxylic acid is treated in an inert solvent with polyethylene glycol that has already been derivatized with amino moieties, after in situ activation.

$CH_3CH_2OC(O)(CH_2)_nC(O)OH$
+
$NH_2CH_2CH_2(OCH_2CH_2)_mOCH_2C(O)NH(CH_2)_pN(CH_3)_2$

1. DCC;
2. NaOH

↓

$HOC(O)(CH_2)_nC(O)NHCH_2CH_2(OCH_2CH_2)_mOCH_2C(O)NH(CH_2)_p$
$C(CH_3)_2$

The amino-derivatized polyethylene glycol is prepared from an N-protected polyethylene glycol amino acid.

$tert-BOCNHCH_2CH_2(OCH_2CH_2)_mOCH_2C(O)-OH + NH_2(CH_2)_pN(CH_3)_2$

DCC/DMAP ↓

$tert—BOCNHCH_2CH_2(OCH_2CH_2)_mOCH_2C(O)—NH(CH_2)_pN(CH_3)_2$

TFA/Basic Column ↓

$NH_2CH_2CH_2_9OCH_2CH_2)_mOCH_2C(O)—NH(CH_2)_pN(CH_3)_2$

The primary amino moiety is deprotected with trifluoroacetic acid and basified before treating with the half-ester.

4.2.9 Formula 9

In the synthesis of the oligomer of Formula 9:

(Formula 9)

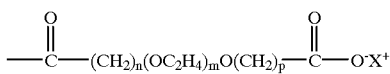

wherein n and p are each independently from 1 to 6, m is from 2 to 25 and $X^+$ is a positive ion, the starting acid is commercially available. It is sometimes desirable to prepare the diacid. To achieve this end, the appropriate modified polyethylene glycol oligomer is treated in an inert solvent with sodium hydride and an ester of a fatty acid bearing a halide moiety at the terminal carbon. The carboxylic acid diester is hydrolyzed in a dilute solution of sodium hydroxide and coupled to the drug moiety after in situ activation. The desired product is separated and purified by column chromatography.

$CH_3CH_2O_2C(CH_3)_nBr$
+
$HOCH_2CH_2(OC_2H_4)_mO(CH_2)_pCO_2CH_2CH_3$

2NaH/THF ↓

$CH_3CH_2O_2C(CH_2)_n(OCH_2CH_2)_mO(CH_2)_pCO_2CH_2CH_3$

NaOH ↓

$HOC(O)(CH_2)_n(OCH_2CH_2)_mO(CH_2)_pC(O)OH$

Drug-OH/$CH_2Cl_2$
DCC/DMAP ↓

$Drug-OC(O)(CH_2)_n(OCH_2CH_2)_mO(CH_2)_pC(O)OH$ where n, m and p are as previously defined.

4.2.10 Formula 10

The synthesis of the oligomer of Formula 10:

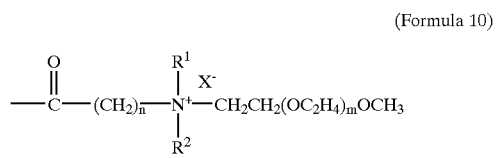

(Formula 10)

wherein n is from 1 to 5, m is from 2 to 25, $X^-$ is a negative ion, and wherein $R^1$ and $R^2$ are each independently lower alkyl, is analogous to the synthesis of the oligomer of Formula 2, with the exception that the amino moiety is quaternized with short-chain aliphatic moieties. It is noted that the methoxy moiety can include other short chain (1 to 6 carbons) aliphatic moieties.

4.2.11 Formula 11

In the synthesis of the oligomers of Formula 11:

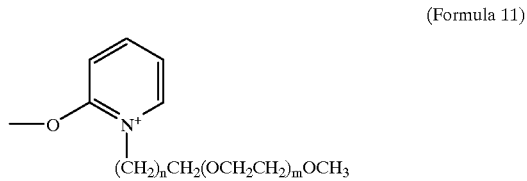

(Formula 11)

wherein n is from 1 to 6, m is from 2 to 25 and $X^-$ is a negative ion, a 2-fluoro- or 4-fluoro-pyridine is treated in an inert solvent with a monomethoxypolyethylene glycol having a terminal carbon bearing a halide, tosylate or mesylate ion. This pyridinium derivative is precipitated and triturated with an appropriate solvent and dried. The salt in an inert solvent is treated with drug, such as paclitaxel or docetaxel, in the presence of a quaternary-salt compound forming base, to yield a polyethylene glycol pyridinium derivative.

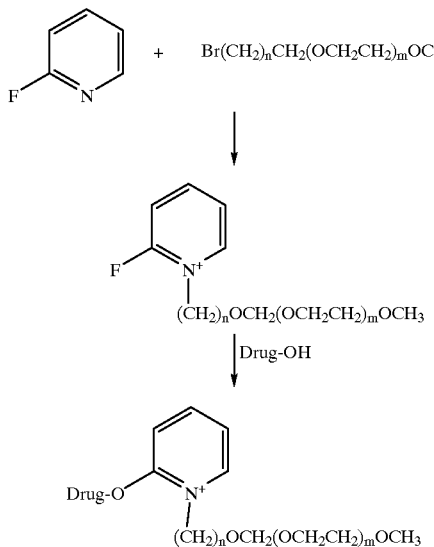

4.2.12 Formula 12

Procedures for preparing the oligomers of Formula 12 are described in the Examples of Section 5 below.

4.2.13 Attachment of PEG Polymers/Oligomers to Taxane Parent

The oligomers are suitably attached to the taxane parent at any of the hydroxyl substituents of the taxane parent. Where the taxane parent is paclitaxel, docetaxel, or an analog thereof, the oligomers are preferably attached at one or more of the following positions: the C-2' hydroxyl group; the C-7 hydroxyl group; and the C-1 hydroxyl group. In a preferred mode, only one oligomer is present, and the oligomer is attached at the C-2' hydroxyl group. It will be appreciated by those of skill in the art that a solution of taxane prodrugs according to the present invention where the taxane is paclitaxel, docetaxel or the like may comprise a mixture of mono-, di-, and/or tri-substituted taxane prodrugs.

The oligomers/polymers of the present invention can be attached to the taxane compound to provide the taxane prodrugs of the invention according to the following general synthetic procedure. The taxane compound is dissolved in a substantially dry organic solvent, e.g., chloroform. Pyridine or another quaternary-compound forming agent is added to the foregoing mixture. Activated oligomer/polymer is added dropwise and the mixture is stirred for 3–5 hours. Then reaction mixture is washed with 1% $H_2SO_4$ and deionized water, dried over $MgSO_4$ and concentrated. The residue is chromatographed on silica gel column, using for example, chloroform-methanol (90%-10%) as developing agent. The fractions containing the desired prodrugs are collected, concentrated, and dried. Product is characterized by TLC, HPLC, NMR, and/or MS.

4.3 Pharmaceutical Compositions and Methods of Use

The pharmaceutical compositions containing the novel prodrugs as active ingredients may be any pharmaceutically acceptable dosage forms known in the art which do not completely diminish the activity of the taxane prodrugs. Examples include oral, injectable or intravenous dosage forms. Each dosage form comprises an effective amount of a prodrug of the invention and pharmaceutically inert ingredients, e.g., conventional excipients, vehicles, fillers, binders, disintegrants, solvents, solubilizing agents, sweeteners, coloring agents and any other active or inactive ingredients which are regularly included in pharmaceutical dosage forms. Suitable oral dosage forms include tablets, capsules, caplets, gelcaps, pills, liquid solutions, suspensions or elixirs, powders, lozenges, micronized particles and osmotic delivery systems. Suitable injectable and IV dosage forms include isotonic saline solutions or dextrose solutions containing suitable buffers and preservatives. Many such dosage forms and vehicles, and listings of inactive ingredients are well known in the art and are set forth in standard texts such as *The Pharmaceutical Codex: Principles and Practice of Pharmaceutics*, $12^{th}$ edition (1994).

The taxane prodrugs of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the taxane prodrugs of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral administration is generally preferred for administration to a human. In some cases, a relatively lower dose is sufficient and, in some cases, a relatively higher dose or increased number of doses may be necessary. Topical application similarly may be once or more than once per day depending upon the usual medical considerations. Advantageously, taxane prodrugs of the present invention may be administered in a single daily dose, or the total daily dosage may be administered in divided doses of two, three or four times daily.

In the methods of the present invention, the taxane prodrugs can form the active ingredient and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the taxane prodrug, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The taxane prodrugs of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The taxane prodrugs of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Taxane prodrugs of the present invention may also be delivered by the use of monoclonal antibodies as individual carriers to which the compound molecules are coupled. The taxane prodrugs of the present invention may also be coupled with soluble polymers, such as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the taxane prodrugs of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, cross-linked or amphipathic block copolymers of hydrogels, polyaspartic acid or polyglutamic acid.

The present invention includes pharmaceutical compositions containing about 0.01 to about 99.5%, more particularly, about 0.5 to about 90% of a taxane prodrug in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the taxane prodrug in a non-toxic liquid vehicle suitable for injection such as aqueous oleaginous medium and sterilizing the suspension or solution.

Alternatively, a measured amount of the taxane prodrug is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the taxane prodrug is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the taxane prodrugs according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

The present invention also provides a method of treating a mammalian subject having a tumor, cancer, or other disease condition responsive to a taxane (e.g., paclitaxel or docetaxel). This treatment method comprises administering to said subject a pharmaceutical composition containing a pharmaceutically effective amount of a taxane-oligomer prodrug according to the present invention. Taxane-responsive diseases which may be treated by the invention include cancers, tumors, malignancies, uncontrolled tissue or cellular proliferation secondary to tissue injury, polycystic kidney disease and malaria. Among the cancers which may be treated are hepatocellular carcinoma, liver metastases, gastrointestinal cancers, lymphoma, leukemia, melanoma, Kaposi's sarcoma, and cancers of the pancreas, kidney, cervix, breast, ovary, brain, prostate, and urogenital carcinoma.

The taxane prodrugs of the invention may be administered by intravenous administration, infusion, non-intravenous injection, intraperitoneally and by injection of a bolus. The taxane prodrugs may also be administered orally to the patient in a suitable dosage form alone or together with an oral bioavailability-enhancing agent. Such bioavailability-enhancing agent may be selected from the group consisting of cyclosporins A through Z, (Me-lle-4)-cyclosporin, dihydro cyclosporin A, dihydro cyclosporin C, acetyl cyclosporin A, genistein and related isoflavonoids, quercetin, calphostin, ceramides, morphine and morphine congeners. Preferred enhancing agents are cyclosporin A, cyclosporin C, cyclosporin D, cyclosporin F, dihydro cyclosporin A, dihydro cyclosporin C, acetyl cyclosporin A, and B cyclodextrin.

Further, the taxane prodrugs of the present invention may be administered alone or with other is chemotherapeutic agents (e.g., anti-cancer agents). Where the paclitaxel-PEG prodrugs of the present invention are administered with other chemotherapeutic agents, the paclitaxel-PEG prodrugs and other chemotherapeutic agents may be administered simultaneously or sequentially. Additionally, the paclitaxel-PEG prodrugs of the present invention may be administered before, after or simultaneously with radiation therapy.

In one aspect, the present invention provides a treatment for cancer comprising administering to a subject a combination of the taxane prodrugs of the present invention and cisplatin. Preferably the cancer is ovarian cancer, and preferably the taxane prodrug comprises paclitaxes and is administered before cisplatin. Paclitaxel has been shown to be effectively administered with cisplatin. Neutropenia has been shown to be a dose limiting effect of coadministration of paclitaxel and cisplatin. Clinical trials have demonstrated that less neutropenia occurs when paclitaxel is administered before cisplatin. For example, while preferred doses of paclitaxel-PEG prodrug are up to 350 mg/m$^2$ followed, by cisplatin (75 mg/m), more preferred doses are paclitaxel-PEG prodrug (25 mg/ml), followed by cisplatin (75 mg/ml) and G-CSF at standard doses (5 μg/kg/d subcutaneously).

5. EXAMPLES

5.1 2'-Succinylpaclitaxel

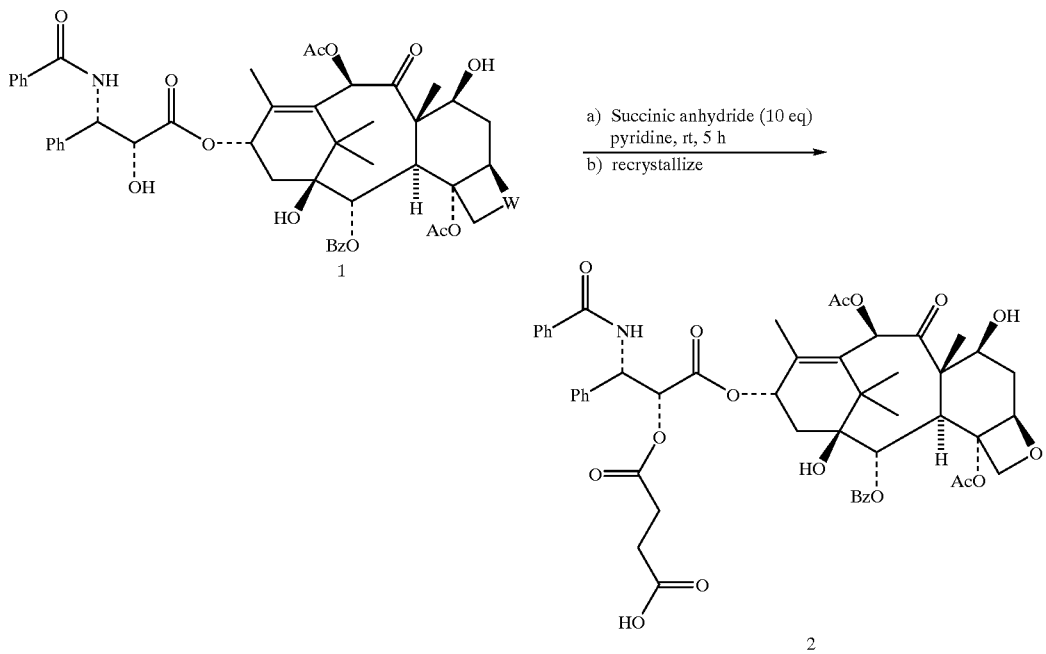

The following protocol is an improved version of the procedure of Deutsch, et. al. To a mixture of 5.00 g (5.86 mmol) of paclitaxel and 5.86 g (58.6 mmol) of succinic anhydride was added 110 mL of anhydrous pyridine. After stirring the resulting solution at room temperature for 5 h, thin layer chromatography (TLC) analysis indicated complete consumption of the paclitaxel. The solvent was removed under reduced pressure by means of rotary evaporation and the residue was dried in vacuo for 2 h. The resulting waxy semisolid was stirred efficiently with 200 mL of water, affording a flocculent white solid, which was collected by suction filtration on a Buchner funnel. The solid was washed with water then allowed to suck dry for 30 mm., then dried at room temperature in vacuo in a dessicator over $P_2O_5$ for 15 h. The white solid was taken up in 30 mL of acetone, then with efficient stirring, 30 ml of water was slowly added. The resulting thick white paste was well-blended for 15 mm, suction filtered through a Buchner funnel rinsing with excess water, and allowed to suck dry for 1 h. The resulting moist white solid was carefully dried at room temperature in vacuo in a dessicator over $P_2O_5$ for 18 h. As the solid became more dry and less coagulated during this drying period, the $P_2O_5$ was replenished and the solid was periodically broken into smaller pieces until a moderately fine powder was obtained (5.29 g, 95% yield). Analytical HPLC analysis indicated this material to be of 97% purity. MS (FAB+) m/z (rel. inten.) 954 ($M^+$, 100), 570 (15), 509 (64).

5.2 2'-Succinamidyl-PEG2-amine-paclitaxel Trifluoroacetate

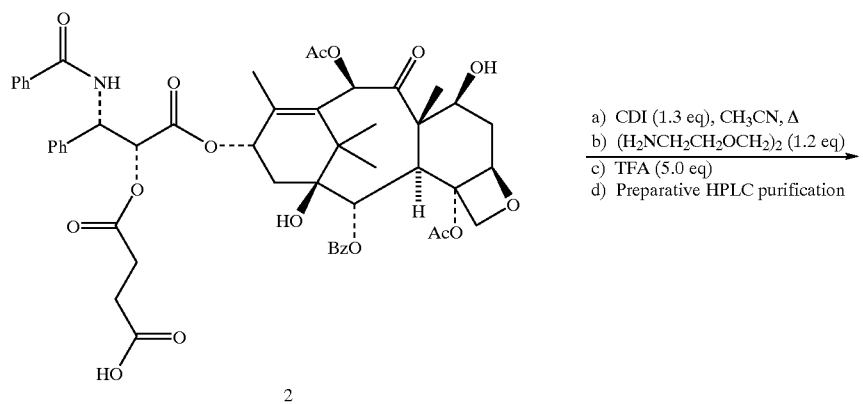

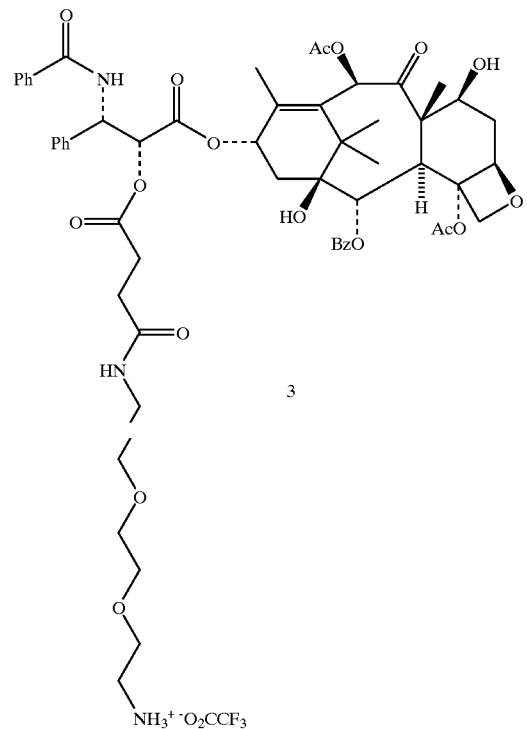

A mixture of 200 mg (0.2 10 mmol) of 2'-succinylpaclitaxel (Compound 2) and 47 mg (0.273 mmol, 95% purity) of 1,1'-carbonyldiimidazole under nitrogen was dissolved in 2.9 mL of anhydrous acetonitrile. A gas outlet needle was inserted through the reaction flask septum such that a moderate flow of nitrogen was maintained to flush out carbon dioxide gas. The reaction vessel was lowered into an oil bath preheated to 48° C., causing gas evolution. After stirring efficiently for 15 min, the reaction vessel was removed from the oil bath and allowed to cool to room temperature. The amount of acetonitrile lost to evaporation was replenished. The nitrogen outlet needle was removed such that a static atmosphere of nitrogen was maintained. A solution of 37 µL (0.252 mmol) of 2,2'-(ethylenedioxy)bis(ethylamine) in 1.4 mL of acetonitrile was added dropwise. After 45 min., a solution of 81 µL (1.05 mmol) of trifluoroacetic acid in 0.7 mL of acetonitrile was added dropwise. The resulting crude reaction solution typically contains a 70–74% yield of the desired trifluoroacetate product (Compound 3), as determined by analytical HPLC analysis.

5.3 Preparative HPLC Purification of Trifluoroacetate (Compound 3)

The product was generally purified by prep HPLC by combining the product-containing fractions.

5.3.1 Improving HPLC Resolution

Medium Scale Reaction

To improve HPLC resolution on a medium scale, the crude reaction solution was diluted by adding water without causing precipitation. Thus, to an aliquot of 3.30 mL of the above reaction solution was slowly added 4.03 mL of water with efficient stirring, consequently affording a solution consisting of 55% water. The resulting slightly hazy mixture was filtered through a 0.45 µm Gelman acrodisc 13 syringe filter, then chromatographed on a Waters 600E HPLC system using a reverse phase Vydac column (22 mm×250 mm, C 18, 300 Å, 10–15µ). The mobile phase was an acetonitrile-water solution containing 0.1% (v/v) trifluoroacetic acid. Major fractions containing desired product of >97% purity were obtained using a gradient elution, from 40:60 to 45:55, acetonitrile:water with 0.1% (v/v) TFA over 30 minutes at a flow rate of 5 mL/mm. Subsequent isocratic elution with 90:10, acetonitrile:water containing 0.1% (v/v) TFA removed unidentified side products in preparation for subsequent chromatographic runs.

For analytical purposes, the purified fractions resulting from the above-described amidation reaction protocol [200 mg (0.210 mmol) scale of 2'-succinylpaclitaxel (2)] were concentrated under reduced pressure by means of rotary evaporation with gradual bath warming to 55° C., then dried in vacuo at room temperature to obtain 170 mg (68% yield) of trifluoroacetate (Compound 3) as an amorphous white solid. $^1$H NMR (300 MHz, CDCl$_3$) δ8.10 (2H, d, J=7.2 Hz), 7.99–7.81 (2H, m), 7.66–7.20 (11H, m), 6.92 (1H, brs), 6.28 (1H, s), 6.07 (1H, t, J=10.0 Hz), 5.86 (1H, dd, J=3.9, 5.0 Hz), 5.65 (1H, d, J=6.9 Hz), 5.42 (1H, d, J=5.4 Hz), 4.94 (1H, d, J=8.2 Hz), 4.36 (1H, m), 4.29 (1H, d, J=8.5 Hz), 4.16 (1H, d, J=8.5 Hz), 3.74 (1H, d, J=6.9 Hz), 3.66–3.04 (16H, m), 2.80–2.60 (2H, in), 2.38 (3H, s), 2.20 (3H, s), 1.84 (3H, s), 1.66 (3H, s), 1.20 (3H, s), 1.13 (3H, s); MS (FAB+) m/z 1084 (M$^+$).

Larger Scale Reaction

A larger scale amidation reaction solution consisting of 1,000 mg (1.05 mmol) of 2'-succinylpaclitaxel (Compound 2), 27 mL total volume was shown to contain 44% of desired trifluoroacetate product (Compound 3) by analytical HPLC analysis. A 10.0 mL aliquot was concentrated under reduced pressure by means of rotary evaporation just to the point of affording a slightly viscous yellow oil. The oil was dissolved by adding 1.0 mL of acetonitrile, filtered through a 0.45 µm Gelman acrodisc 13 syringe filter, then chromatographed on a Waters 600E HPLC system using a reverse phase Vydac column (50 mm×250 mm, C18, 300 Å, 10–15µ). The mobile phase was an acetonitrile-water solution containing 0.1% (v/v) trifluoroacetic acid. Major fractions containing desired product of >97% purity were obtained using a gradient elution, from 40:60 to 45:55, acetonitrile:water with 0.1% (v/v) TFA over 30 minutes at a flow rate of 26 mL/min. Subsequent isocratic elution with 90:10, acetonitrile:water containing 0.1% (v/v) TFA removed unidentified side products in preparation for subsequent chromatographic runs.

The fractions determined by analytical HPLC analysis to be of high purity were combined with analogous preparative HPLC runs to provide a combined solution of 870 mL total volume containing trifluoroacetate (Compound 3) of >97% purity. The solution was used directly (without concentration) in the ion exchange chromatography step.

5.4 Stability of Trifluoroacetate (Compound 3)

It was observed that several trifluoroacetate product fraction solutions obtained from a preparative HPLC run initially of an average purity of 98.8% changed to an average of 97.4% purity after storage at 8° C. for 16 days, as determined by analytical HPLC analysis.

5.4.1 Determination of Aqueous Solubility of Trifluoroacetate (Compound 3)

To a sample of 2.5 mg of trifluoroacetate (Compound 3) in a small vial was added 200 µL of deionized water. The vial was capped and the resulting mixture was ultrasonicated for 15 minutes. The resulting cloudy mixture was filtered through a 0.45µ Gelman acrodisc 13 syringe filter. The filtrate was weighed (140 mg) and was lyophilized to provide 1.4 mg of a white fluffy solid. Thus, assuming that the aqueous solution is of density 1.00, the water solubility of trifluoroacetate (Compound 3) is 7.4 mg/mL (i.e. 1.4 mg/0.190 mL).

5.5 Ion Exchange Chromatography of Trifluoroacetate Anion for Acetate Anion: Acetate Prodrug (Compound 4)

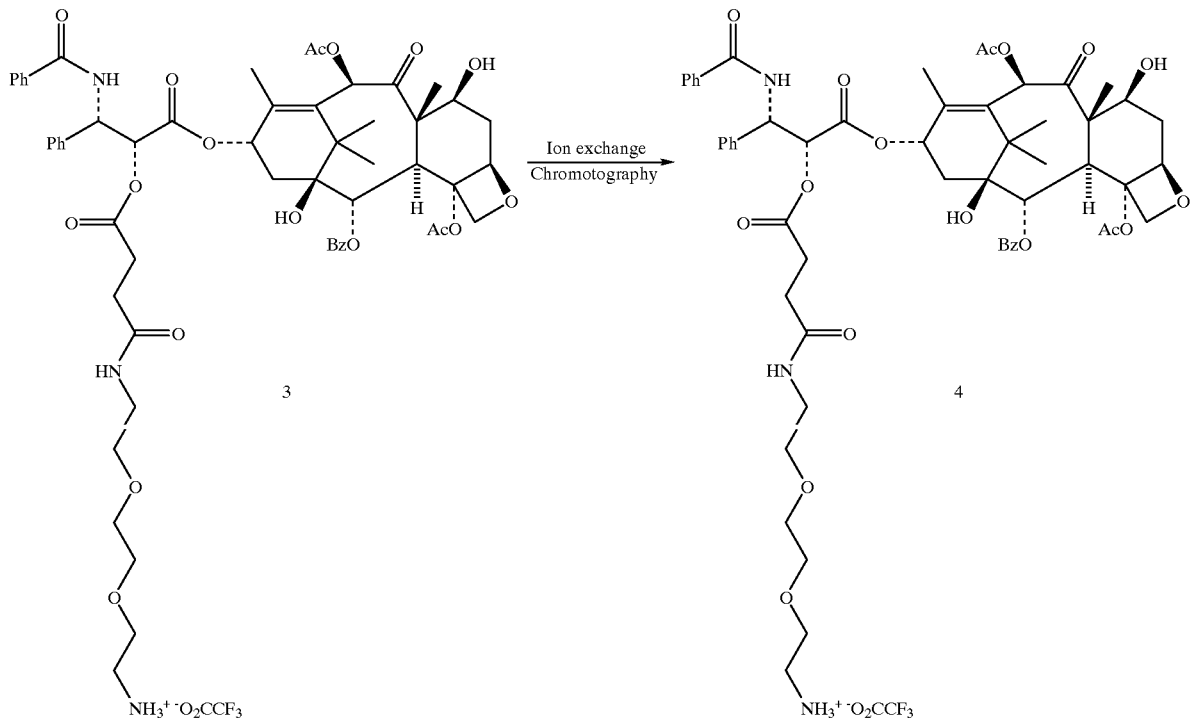

For preparative purposes, fraction solutions of trifluoroacetate (Compound 3) of >97% purity obtained from a preparative HPLC purification protocol described above were combined and taken on directly to ion chromatography without concentration. For example, combined preparative HPLC fractions of 870 mL total volume theoretically containing 0.462 mmol of substrate and containing 11.3 mmol of TFA (0.1% (v/v)) was used for the following ion exchange protocol:

A 92 g portion of DOWEX® 1×8–400 (strongly basic, chloride form) ion exchange resin was washed three times with 270 mL each of deionized water, each time decanting away the yellow suspended matter and the bulk of the rinse water. To obtain the resin in its acetate form, the resulting slurry was stirred with a solution of 1,882 g of NaOAc.3H$_2$O in 4.00 L of deionized water for 1.0 h. The resin was collected by suction filtration on a Buchner funnel and washed several times with a total of 1.84 L of deionized water. The resin was washed two times with 750 mL each of 0.013 M HOAc (aq) [i.e. 0.1% (v/v) HOAc, by analogy to 0.1% (v/v) TFA used in the preparative HPLC protocols], suction filtered on a Buchner funnel, then allowed to suck dry for 10 min. The resin was suspended in 0.013 M HOAc (aq), poured into a glass flash chromatography column, then eluted using gentle air pressure with 200 mL of 0.013 M HOAc (aq), thus giving a 10 cm high×3.8 cm diameter resin column, which was then topped off with ca. 4 cm of sand. The column was then eluted with 250 mL of acetonitrile, then with 250 mL of 0.0 13 M HOAc (aq). The 870 mL volume of the trifluoroacetate (3) solution was made to be 0.0 13 M in HOAc by the addition of a solution of 0.63 mL of glacial acetic acid in 10 mL of acetonitrile with efficient stirring. The solution was applied to and eluted through the column using gentle air pressure. Fraction collection was commenced immediately using 50 mL test tubes. Once the entire 870 mL of solution had completely passed into/through the resin, the column was further eluted with 0.013M HOAc (aq). The fractions containing product of >97% purity (as determined by analytical HPLC analysis at 210 nm) were combined and concentrated under reduced pressure by means of rotary evaporation with gradual bath warming to 55° C. and dried in vacuo at room temperature for 16 h to provide an off-white amorphous residue. The residue was scraped with a spatula from the flask into a fine amorphous powder. The remnants not scraped out of the flask could be further procured without alteration of product purity by transferring to a smaller flask with the aid of a minimal amount of 0.013M HOAc (aq) as solvent, concentrating as described above, then scraping with a spatula to provide additional product, which was combined and dried at room temperature in vacuo in a dessicator over P$_2$O$_5$ for 24 h to provide acetate prodrug (Compound 4) (293 mg, 24% unoptimized yield overall of material of >97% purity) as a yellow powder. Combination of the fractions of <97% purity in a manner similar to the method described above afforded 146 mg (12% unoptimized yield) of additional acetate (Compound 4). Analyses of the products by analytical ion chromatography [Quantitative Technologies, Inc., (QTI)] did not show the presence of any trifluoroacetic acid (TFA analysis: below detection limit of 100 ppm). mp 114–117° C.; $^1$H NMR (300 MHz, CDCl$_3$) δ8.11(2H, d, J=7.2 Hz), 7.85 (2H, d, J=7.7 Hz), 7.62–7.36 (11H, m), 6.29 (1H, s), 6.11 (1H, t, J=10.0 Hz), 5.87 (1H, dd, J=3.9, 4.4 Hz), 5.65 (1H, d, J=6.9 Hz), 5.44 (1H, d, J=4.9 Hz), 4.95 (1H, d, J=9.5 Hz), 4.38 (1H, m), 4.28 (1H, d, J=8.5 Hz), 4.18 (1H, d, J=8.2 Hz), 3.76 (1H, d, J=6.4 Hz), 3.63–3.34 (16H, m), 3.04 (2H, brs), 2.75 (2H, in), 2.53 (2H, m), 2.40 (3H, s), 2.20 (3H, s), 2.01 (3H, s), 1.87 (3H, s), 1.67 (3H, s), 1.20 (3H, s), 1.13 (3H, s); MS (FAB+) m/z (rel. inten.) 1084 (M$^+$).

5.6 General Solubility of Acetate (Compound 4)

Acetate (Compound 4) is highly soluble in $CDCl_3$ and sparingly soluble in diethyl ether and in hexanes. Three separate samples of 3.0 mg each of acetate (Compound 4) afforded a homogeneous solution in 81 $\mu$L of 100% anhydrous ethanol, in 81 $\mu$L of acetone, and in 81 $\mu$L of 0.5 M aqueous acetic acid. Thus, the solubility in each of these three solvents must be some value equal to or greater than 37 mg/mL (i.e. 3.0 mg/0.08 1 mL).

5.7 Determination of Aqueous Solubility of Acetate (Compound 4) by Mass

To a sample of 10.0 mg of acetate (Compound 4) in a small vial was added 176 $\mu$L of deionized water. The vial was capped and the resulting mixture was ultrasonicated for 15 minutes. The resulting liquid was shown to contain acetate (Compound 4) in 98.7% purity by analytical HPLC analysis at 210 nm. The liquid was filtered through a 0.45$\mu$ cellulose acetate syringe filter. The mass (76 mg) of a known volume (75 $\mu$L) of the filtrate was measured to determine that the density of the solution was 1.01 g/mL. The filtrate was shown to contain acetate (Compound 4) in 98.8% purity by analytical HPLC analysis at 210 nm. A 118 mg quantity of the filtrate was lyophilized to provide 6.4 mg of an off-white fluffy solid. Thus, by this method the water solubility of acetate (Compound 4) was determined to be 55 mg/mL (i.e. 6.4 mg/0.117 mL).

5.8 Determination of Aqueous Solubility of Acetate (Compound 4) by Analytical HPLC To a sample of 10.0 mg of acetate (Compound 4) in a small vial was added 150 $\mu$L of deionized water. The vial was capped, vortexed for 3 mm., and ultrasonicated for 15 minutes. The resulting viscous pale yellow/orange mixture was slowly and carefully taken up into a 1 mL syringe and then firmly filtered through a 0.45$\mu$ cellulose acetate syringe filter, thus affording a viscous homogeneous yellow/orange solution. A 75 $\mu$L portion of the filtrate was diluted 88-fold with acetonitrile and then analyzed by analytical HPLC at 229 nm and 270 nrm. The area under the curve observed at 229 nm and 270 nm was respectively compared to both a 3-point calibration curve obtained at 229 nm ($r^2$=0.99999) and a 5-point curve obtained at 270 nm ($r^2$=0.99996). Thus, by this method, the water solubility of acetate (Compound 4) was determined to be 40.1 mg/mL (at 229 nm) and 39.7 mg/mL (at 270 nm).

5.9 Chemical Hydrolysis Behavior of Acetate (Compound 4)

A sample of solid acetate (Compound 4) was dissolved (ca. 1 mg/mL) in wet acetonitrile (nonanhydrous due to exposure to humid air). Over the course of 26 days at room temperature, acetate (Compound 4) smoothly converted quantitatively into paclitaxel (1) with no significant side product formation, as observed by analytical HPLC analysis (see FIG. 1).

5.9.1 Chemical Hydrolysis Behavior of Acetate (Compound 4) at Various pH

To many 13 mm×100 mm glass test tubes was added 5.15 $\mu$L each of an 8.741×$10^{-4}$ M aqueous solution of acetate prodrug (Compound 4). To each tube was then added 295 $\mu$L of aqueous solutions of phosphate buffered saline (PBS) of pH 8.00, 7.40, 7.00 and 5.80 and an acetic acid/formic acid buffered solution of pH 2.00. The tubes were capped and incubated at 37° C. in a reciprocal water bath shaker. After incubation for various appropriate time intervals, a test tube was removed from the shaker, 900 $\mu$L of acetonitrile was added, and the sample was vigorously vortexed for 3 minutes. The resulting solutions were analyzed by analytical HPLC to generate hydrolysis rate data (see table and graphs, below).

5.10 In Vitro Prodrug Hydrolysis of Acetate (Compound 4)

Figure 2:
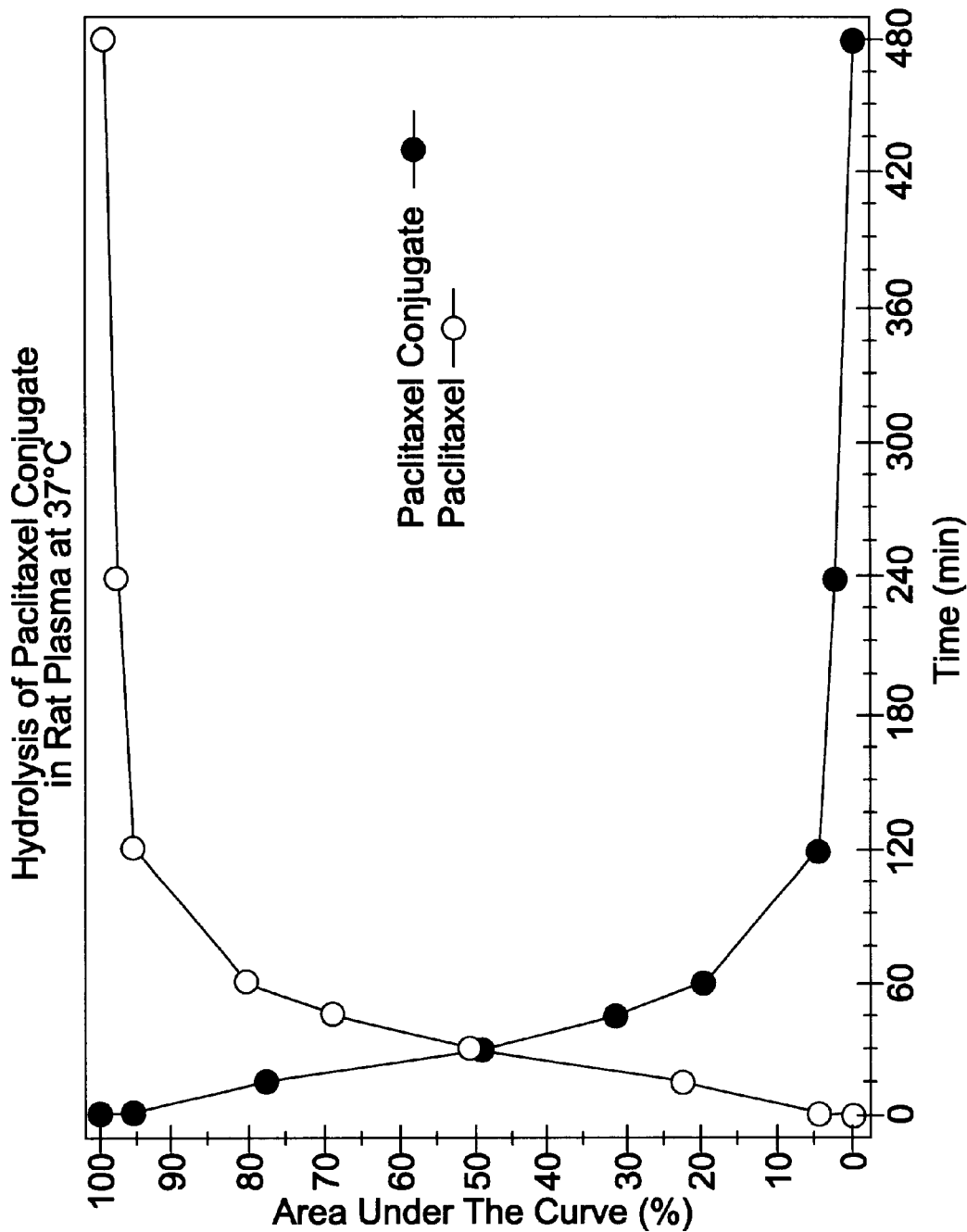
FIG. 2 shows in vitro hydrolysis of acetate (Compound 4) in heparinized rat plasma and demonstrates that most of the taxane prodrug rapidly hydrolyzes within two hours to provide free paclitaxel.

To nine 13 mm×100 mm test tubes was added 5.15 $\mu$L each of an 8.741×$10^{-4}$ M aqueous solution of acetate prodrug (Compound 4). To each tube was then added 295 $\mu$L of freshly obtained heparinized rat plasma from an adult male Sprague Dawley rat (CD) (source Charles River; Raleigh, N.C.). The tubes were capped and incubated at 37° C. in a reciprocal water bath shaker. After incubation for various time intervals, a test tube was removed from the shaker, 900 $\mu$L of acetonitrile was added, the sample was vigorously vortexed for 3 minutes and then cooled to $-12°$ C. for between 30 and 90 minutes. The samples were centrifuged at 25° C. for 10 minutes at 1,600 g and the resulting clear colorless supernatant solution was analyzed by analytical HPLC (see FIG. 2).

5.11 2'-Succinamidyl-PEG2-amine-paclitaxel Acetate

A mixture of 200 mg (0.210 mmol) of 2'-succinylpaclitaxel (Compound 2) and 47 mg (0.273 mmol) of 1,1'-carbonyldiimidazole under nitrogen was dissolved in 5 mL of anhydrous acetonitrile. The reaction vessel was lowered into an oil bath preheated to 48° C., causing gas evolution. After stirring for 15 min, the reaction vessel was allowed to cool to room temperature. A solution of 37 $\mu$L (0.252 mmol) of 2,2'-(ethylenedioxy)bis(ethylamine) in 2 mL of acetonitrile was added dropwise, then after 1 h a solution of acetic acid (1.05 mmol) in I mL of acetonitrile was added. The resulting crude reaction solution obtained by this method typically contains a 75% yield of desired acetate product, as determined by analytical HPLC analysis.

5.12 Preparative HPLC Purification of 2'-Succinamidyl-PEG2-amine-paclitaxel Acetate The crude compound from Example 5.11 was chromatographed on a Waters Prep LC 4000 system, using a reverse phase Vydac column (22 mm×250 mm, C18, 300□, 10–15$\mu$). The product was purified by combining the product-containing fractions obtaining from preparative HPLC. Major fractions containing desired product (>97% purity) were obtained using a gradient elution, from 30:70 to 95:5, acetonitrile:water with 0.1%(v/v) acetic acid over 35 min. The purified fraction were concentrated under reduced pressure by means of rotary evaporation, then lyophilized to obtain white solid. MS (FAB+) m/z 1084 ($M^+$).

5.13 2'-Glutaramidyl-PEG2-amine-paclitaxel Acetate

2'-Glutarylpaclitaxel is synthesized using the procedure described above in Example 5.1 by substituting glutaric anhydride for succinic anhydride. 2'-Glutaramidyl-PEG2-amine-paclitaxel acetate (Compound 5) is then synthesized using the procedure described above in Example 5.1 1 by using 2'-glutarylpaclitaxel instead of 2'-succinylpaclitaxel as a starting material. The chemical structure of compound 5 is shown below.

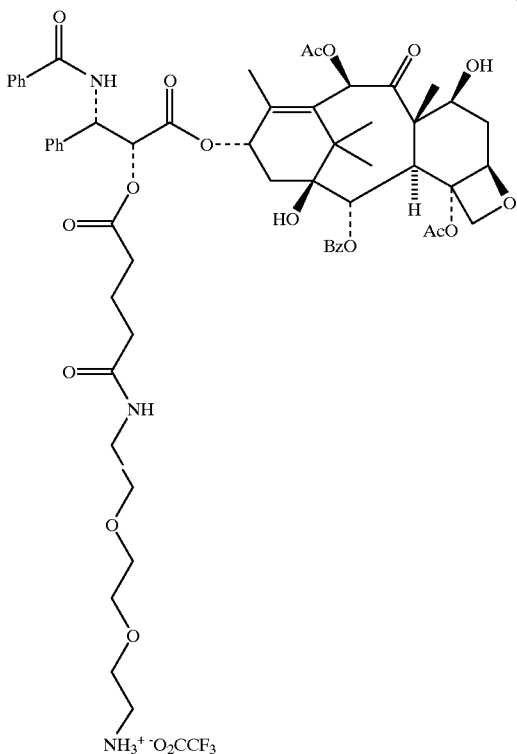

5.14 Preparative HPLC Purification of 2'-Glutaramidyl-PEG2-amine-paclitaxel Acetate Preparative HPLC purification of 2'-glutaramidyl-PEG2-amine-paclitaxel acetate is performed using the procedure described above in Example 5.12.

5.15 Effect of Compounds of the Present Invention on the NIH:OVCAR-3 Cell Line

Figure 3:
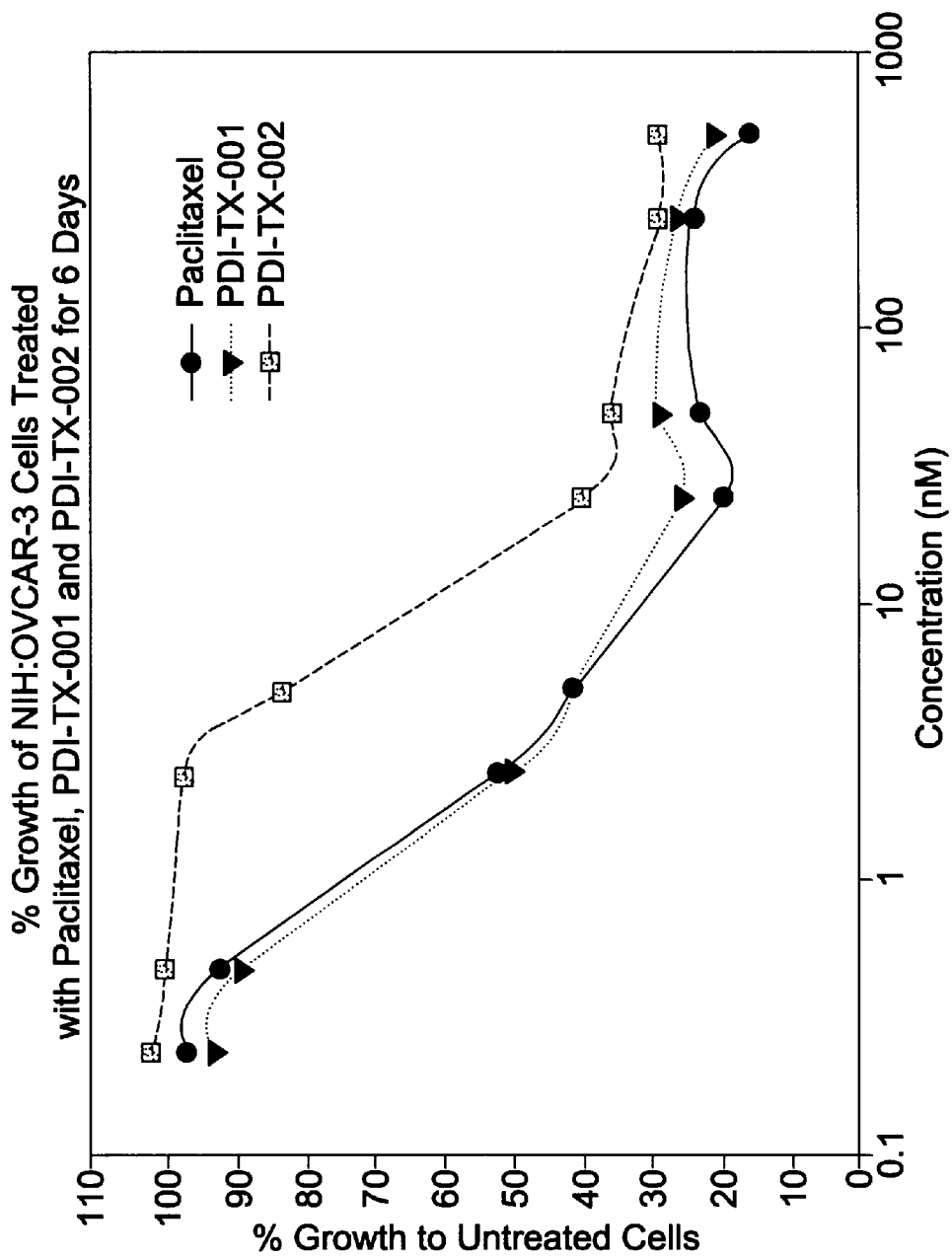
FIG. 3 shows percent growth of NIH:OVCAR-3 cells treated with compounds of the present invention in comparison with paclitaxel.

The purpose of this experiment was to investigate the effect of a full dose response of Paclitaxel (tested for comparison purposes only, not a compound of the present invention), TX-001 (Compound 4, described above in Example 5.5), and TX-002 (Compound 5, described above in Example 5.13) on the NIH:OVCAR-3 cell line. NIH:OVCAR-3 cells, which are a human ovarian cancer cell line, were removed from a T75 flask by versene and counted via a hemacytometer. The cells were then pelleted by centrifugation (1000 RPM for 10 minutes). The supernatant was removed and fresh media (RPMI 1640 w/10%FCS and 1% L-glutamine) was added to bring cell concentration to 10,000 cells/mL. Then 0.1 mL (1000 cells) of the 10,000 cell/mL solution was added to individual wells of a 96 welled flat bottom plate. This plate was then placed overnight in a 37° C. with 5% $CO_2$ incubator to allow cells time to adhere to bottom of wells. The next day Paclitaxel, TX-001, and TX-002 were diluted in fresh media to the following concentrations: 1000, 500, 200, 50, 10, 5, 1 and 0.5 nM. Next 0.1 mL of the appropriate drug concentration was added to appropriate column of 96 welled plate (n=8) making final concentrations of 500, 250, 50, 25, 5, 2.5, 0.5, and 0.25 nM. One column on each plate received 0.1 mL of fresh media and served as the untreated control. These plates were then placed in the 37° C. with 5% $CO_2$ incubator for 6 days. After 6 day incubation, all wells were aspirated and plates were placed in a −70° C. freezer for 2 hours. Also an appropriate number of cells were removed from another T75 flask in the same fashion as mentioned above but this time after centrifugation the supernatant was removed and the tube was placed in a −70° C. freezer for 2 hours. The plates and tube were thawed at room temperature and then the CyQuant assay (Molecular Probes) was performed. The tube was resuspended with an appropriate amount of the CyQuant GR dye/cell lysis buffer and diluted accordingly to create a standard curve. Next 0.2 mL of each standard concentration was placed in duplicate in a new 96 well plate. This plate was then placed in the dark for 3 minutes. Finally all wells of the 96 well plates that were previously frozen and thawed received 0.2 mL of CyQuant GR dye/cell lysis buffer and as well were placed in dark for 3 minutes. The fluorescence was then measured at 485 nm excitation and 538 nm emission. Cell number per each well was then calculated from the standard curve. Means were calculated for each concentration of drug and then were divided by the mean of the untreated wells for each particular plate. The results are shown in FIG. 3 and expressed in % growth to untreated cells.

5.16 Effect of Compounds of the Present Invention on the Production of Activated Caspase-3 by the NIH:OVCAR-3 Cell Line The purpose of this experiment was to investigate the effect of 50 nM Paclitaxel, TX-001, and TX-002 on the production of activated Caspase-3 by the NIH:OVCAR-3 cell line. 7 T75 flasks with approximately 70–80% NIH:OVCAR-3 cell confluence were used for this experiment. Each flask was rinsed with 5 mL of PBS then 15.0 mL of appropriate drug were added to each flask. These flasks were then placed in a 37° C. with 5% $CO_2$ incubator until desired time point was achieved. Each T75 flask was then 0.05% Trypsin treated and cells were counted via a hemacytometer. The cells were then pelleted by centrifugation (1000 RPM for 10 minutes). The amount of active Caspase-3 was then determined by the Caspase-3 Fluorometric Assay (R&D Systems). The supernatant was removed from the pelleted cells and 25 μL of cold Cell Lysis Buffer is added for every 1,000,000 cells/mL. This cell lysate was incubated on ice for 10 minutes and then 50 μL from each condition is added in duplicate to a 96 well flat bottom plate. Next 50 μL of 2×Reaction Buffer and 5 μl of Caspase-3 fluorogenic substrate (DEVD-AFC) were added to each well. The plate was then placed in a 37° C. with 5% $CO_2$ incubator for 1.5 hours. Finally the fluorescence was then measured at 400 nm excitation and 505 nm emission. Data was then plotted as active Caspase-3 Fluorescence as illustrated in FIG. 4.

5.17 Evaluation of the Anti-tumor Activity of Compounds 4 and 5 Against a Series of Human Tumor Cell Lines In Vitro HT-1080 and HT-1080/DR4 (MRP/LRP positive) fibrosarcoma cell lines (1,2) were obtained from Dr. Y. Rustum, Roswell Park Cancer Institute, Buffalo, N.Y. The A121 ovarian cell line (3) was provided by Dr. Kent Crickard, Buffalo General Hospital, Buffalo, N.Y. The MDA435/LCC6-WT and MDR1 transfected cell lines (4) were provided by Dr. R. Clarke, Lombardi Cancer Center, Georgetown University School of Medicine. Cell lines were propagated as monolayers in RPMI-1640 containing 5% FCS, 5% NuSerum IV, 20 mM HEPES, 2 mM L-glutamine at 37° C. in a 5% $CO_2$ humidified atmosphere.

Paclitaxel, which was used for comparison purposes and is not a compound of the present invention, was provided by Dr. I. Ojima, SUNY at Stonybrook. TX-001 (Compound 4) and TX-002 (Compound 5) (CD#20027 and 20028 respectively) were provided by NOBEX.

Paclitaxel was solubilized in 100% DMSO. TX-001 and 002 were solubilized in sterile $H_2O$ acidified with 10% 1 N HCl. For the first experiment, 4.0 mM stocks of TX-001 and 002 were prepared. Solutions of TX-001 and TX-002 contained clear needle-like and cast-like precipitates and were fairly viscous (Experiment 1). For the second experiment (Experiment 2), less concentrated stock solutions (0.4 mM) of each compound were prepared in sterile $H_2O$ acidified with 10% 1 N HCl. The same type of precipitates were noted, however neither solution was viscous. All compounds were further diluted in RPMI-1640 containing 10 mM HEPES.

Assessment of cell growth inhibition was determined in 96 well microtiter plates according to the method of Skehan et al., "New Colorimetric Cytotoxicity Assay for Anticancer-Drug Screening, Articles 82(13):1107–1112 (1990). Briefly, cells were plated with 400–1800 cells/well in 96 well plates and incubated at 37° C. 15–18 hr prior to drug addition to allow for cell attachment. Each cell line was exposed to 12 concentrations of compound (a 6 log range), 5 replicate data points per compound concentration. Cells were exposed to compound concentrations ranging from 0.003 to 1000 nM for paclitaxel and 0.03 to 10000 nM for TX-001 and TX-002. Cells were cultured for a total of 3–4 cell doublings (72–96 h). Assays were terminated with 100 µl of ice-cold 50% TCA. After 1 hr at 4° C., plates were washed 5 times with tap water to remove TCA, low-molecular-weight metabolites and serum proteins. 50 µl of 0.4% sulforhodamine B (SRB) was added to each well. Following a five minute incubation at room temperature, plates were rinsed 5 times with 0.1% acetic acid and air dried. Bound dye was solubilized with 10 mM Tris Base (pH 10.5) for 5 min on a gyratory shaker. Optical density was measured at 570 nm.

Data were fit with the Sigmoid-Emax concentration-effect model (N. H. G. Holford and L. B. Scheiner, "Understanding the dose-effect relationship: Clinical applications of pharmacokinetic-pharmacodynamic models," *Clin. Pharmacokin.* 6:429–453 (1981)) with nonlinear regression, weighted by the reciprocal of the square of the predicted response. The fitting software was developed at RPCI with Microsoft FORTRAN, and uses Marquardt algorithm (D. W. Marquardt, "An algorithm for least squares estimation of nonlinear parameters," J. Soc. Ind. Appl. Math. 11:431–441) as adapted by Nash (J. C. Nash, *Compact Numerical Method for Computers: Linear Algebra and Function Minimization*, New York: John Wiley & Sons, 1979) for the nonlinear regression. The concentration of drug that resulted in 50% growth inhibition ($IC_{50}$) was calculated and is shown in Table I below.

TABLE I

Effect of Paclitaxel, TX-001 and TX-002 on Human Tumor Cell Growth

| | | IC50 nM (±S.E.)[1] | | | | |
|---|---|---|---|---|---|---|
| Compound | Experiment | A121 | LCC6-WT | LCC6-MDR | HT-1080 | HT-1080-DR4 |
| Paclitaxel | 1 | 11 ± 0.5 | 4.7 ± 0.5 | 434 ± 28 | 4.5 ± 0.2 | 4.9 ± 0.4 |
| | 2 | 14 ± 1.3 | 6.0 ± 2.0 | 391 ± 52 | 5.7 ± 0.3 | 7.7 ± 0.1 |
| TX-001 | 1 | 13 ± 0.5 | 4.9 ± 0.5 | 337 ± 20 | 4.5 ± 0.4 | 8.9 ± 0.4 |
| | | | 2.7 ± 0.4[2] | 269 ± 31[2] | | |
| | 2 | 37 ± 1.2 | 13 ± 0.5 | 404 ± 63 | 19 ± 0.7 | 36 ± 1.5 |
| TX-002 | 1 | 48 ± 3.0 | 18 ± 1.1 | 1073 ± 45 | 22 ± 0.9 | 32 ± 1.5 |
| | | | 16 ± 2.0[2] | 879 ± 78[2] | | |
| | 2 | 171 ± 8.8 | 38 ± 4.6 | 1798 ± 168 | 49 ± 6.5 | 54 ± 5.3 |

[1]Human tumor cell lines: A121-ovarian carcinoma; LCC6-WT-breast carcinoma, LCC6-MDR1-Pgp transfected line; HT-1080-fibrosarcoma, HT-1080-DR4-doxorubicin selected MDR (MRP/LRP phenotype).
[2]4.0 mM stock solutions that had been stored at 4° C. for 7 days were used.

TX-001, TX-002 and paclitaxel were evaluated for tumor cell growth inhibition using a panel of human tumor cell lines including A121 ovarian, breast tumor cell lines LCC6 and the LCC6-MDR1 variant, which was transfected with the MDR1 gene and over-expresses P-glycoprotein. These compounds were also evaluated against an MRP/LRP expressing, multidrug resistance HT1080/DR4 human sarcoma cell line.

TX-001 and TX-002 are active agents against a number of human tumor cell types, with IC50 values ranging between 2.7–1798 nM (Table 1). TX-001 appears to be more potent than TX-002 with a growth inhibition profile nearly identical to that of paclitaxel.

Resistance ratios (IC50 resistant cell line/IC50 parental line) in the LCC6-MDR1 variant line which overexpresses Pgp were similar for the three compounds tested. They ranged from 65–92 fold for paclitaxel, 30–100 fold for TX-001 and 47–60 fold for TX-002. Resistance ratios in the MRP/LRP expressing mutidrug resistant HT1080/DR4 cell line were also similar ranging from 1.1–1.4 fold for paclitaxel, 1.9–2.0 fold for TX-001 and 1.1–1.5 fold for TX-002.

Re-testing of TX-001 and TX-002 from stock solutions which had been stored at 4° C. for 7 days, demonstrated a small increase of activity in LCC6 and LCC6-MDR1 cells. Testing with non-viscous stock solutions (0.4 mM) of TX-001 and TX-002 showed slightly less potency in all of the cell lines tested as compared to the initial results and repeat testing results of the 4.0 mM stock solutions.

Both TX-001 and TX-002 are active agents with TX-001 being the more potent.

The foregoing embodiments and examples are illustrative of the present invention and are not to be construed as limiting thereof. The invention is defined by the following claims, with equivalents of the claims to be included therein.

That which is claimed is:

1. A taxane prodrug comprising a taxane joined by a hydrolyzable bond to an oligomer having the following structure:

(Formula 12)

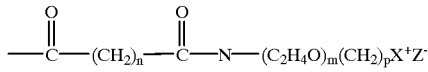

wherein n is from 1 to 12, m is from 2 to 25, p is from 2 to 12, $X^+$ is a positive ion and $Z^-$ is a negative ion.

2. The taxane prodrug according to claim 1, wherein the taxane is paclitaxel.

3. The taxane prodrug according to claim 2, wherein the oligomer is joined to the 2' position of the paclitaxel.

4. The taxane prodrug according to claim 1, wherein the taxane is docetaxel.

5. The taxane prodrug according to claim 1, wherein the taxane is a paclitaxel analog that retains some or all of the therapeutic activity of paclitaxel.

6. The taxane prodrug according to claim 1, wherein the taxane is derivatized by 2, 3 or 4 of the oligomers of Formula 12.

7. The taxane prodrug according to claim 1, wherein the positive ion is selected from tho group consisting of $NH_3^+$ and trisubstituted sulfur and the negative ion is selected from the group consisting of chloro anion, bromo anion, iodo anion, phosphate anion, acetate anion, trifluoracetate anion, carbonate anion, sulfate anion, and mesylate anion.

8. The taxane prodrug according to claim 1, wherein n is from 2 to 4.

9. The taxane prodrug according to claim 8, wherein m is from 2 to 10 and p is from 2 to 4.

10. The taxane prodrug according to claim 1, wherein the taxane prodrug has an aqueous solubility that is greater than 30 mg/ml.

11. A pharmaceutical composition comprising:
a taxane prodrug according to claim 1; and
a pharmaceutically acceptable carrier.

12. A method of treating a mammalian subject having a taxane-responsive disease condition comprising administering to the subject an effective disease treating amount of the taxane prodrug according to claim 1.

13. The method according to claim 12, wherein the administering of the taxane prodrug comprises orally administering the taxane prodrug.

14. The method according to claim 12, wherein the disease condition is cancer.

15. The method according to claim 12, wherein the disease condition is ovarian cancer or breast cancer.

16. The method according to claim 15, further comprising co-administering cisplatin or doxorubicin with the taxane prodrug.

17. The method according to claim 16, wherein the co-administering of cisplatin or doxorubicin with the taxane prodrug comprises simultaneously co-administering cisplatin with the taxane prodrug.

18. The method according to claim 16, wherein the co-administering of cisplatin or doxorubicin with the taxane prodrug comprises sequentially co-administering cisplatin with the taxane prodrug.

19. A taxane prodrug comprising a taxane joined by a hydrolyzable bond to an oligomer having the following structure:

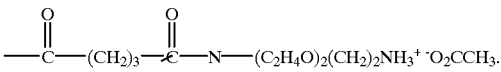

20. The taxane prodrug according to claim 19, wherein the taxane is paclitaxel.

21. The taxane prodrug according to claim 20, wherein the oligomer is joined to the 2' position of the paclitaxel.

22. The taxane prodrug according to claim 19, wherein the taxane is docetaxel.

23. The taxane prodrug according to claim 19, wherein the taxane is a paclitaxel analog that retains some or all of the therapeutic activity of paclitaxel.

24. The taxane prodrug according to claim 19, wherein the taxane is derivatized by 2, 3 or 4 of the oligomers.

25. A pharmaceutical composition comprising:
a taxane prodrug according to claim 19; and
a pharmaceutically acceptable carrier.

26. A method of treating a mammalian subject having a taxane-responsive disease condition comprising administering to the subject an effective disease treating amount of the taxane prodrug according to claim 19.

27. The method according to claim 26, wherein the administering of the taxane prodrug comprises orally administering the taxane prodrug.

28. The method according to claim 26, wherein the disease condition is cancer.

* * * * *

UNITED STATES PATENT AND TRADEMARK OFFICE
CERTIFICATE OF CORRECTION

PATENT NO. : 6,541,508 B2
DATED : April 1, 2003
INVENTOR(S) : Ekwuribe et al.

It is certified that error appears in the above-identified patent and that said Letters Patent is hereby corrected as shown below:

Column 2,
Line 25, should read -- infusion time and premedicating patients with immunosup- --

Column 12,
Line 63, should read -- Drug—OC(O)(CH$_2$)$_n$C(O)NH$_2$CH$_2$CH$_2$CH$_2$(OC$_2$H$_4$)$_m$NH$_2$ --

Column 13,
Line 42, should read -- (CH$_3$)$_3$COC(O)NH$_2$(CH$_2$)$_p$NHCH$_2$CH$_2$(OC$_2$H$_4$)$_m$NH$_2$ --
Line 60, should read (Formula 8)

Column 14,
Line 1, should read

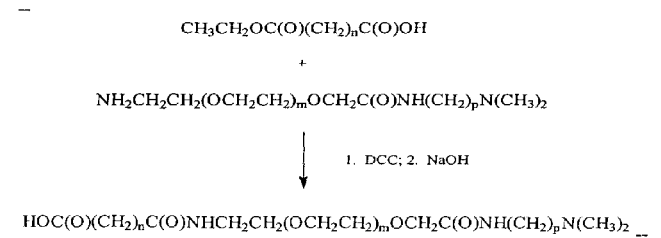

Line 15, should read

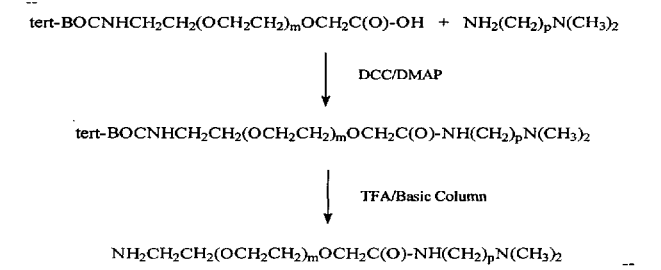

UNITED STATES PATENT AND TRADEMARK OFFICE
CERTIFICATE OF CORRECTION

PATENT NO.    : 6,541,508 B2
DATED         : April 1, 2003
INVENTOR(S)   : Ekwuribe et al.

It is certified that error appears in the above-identified patent and that said Letters Patent is hereby corrected as shown below:

Column 20,
Line 16, should read -- be administered alone or with other chemotherapeutic --
please replace the structures with

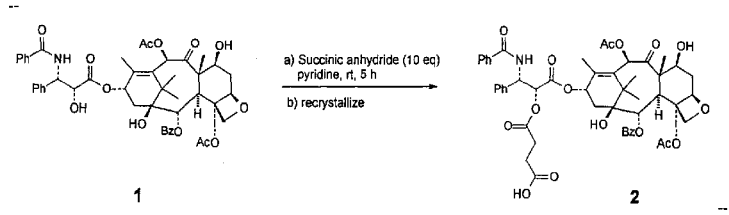

Column 26,
Please replace the structures with

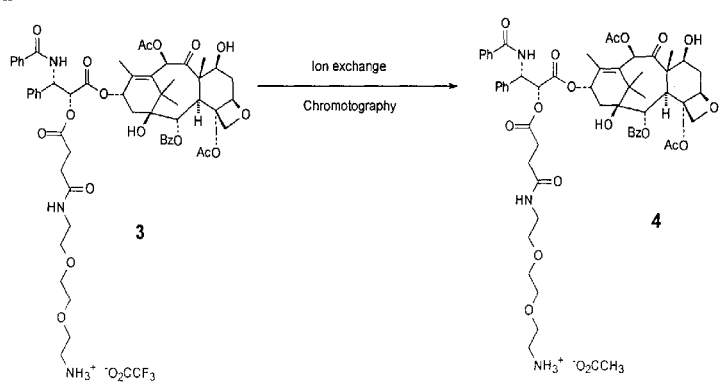

Column 28,
Line 48, should read -- phase Vydac column (22 mm x 250 mm, C18, 300Å, --

UNITED STATES PATENT AND TRADEMARK OFFICE
CERTIFICATE OF CORRECTION

PATENT NO. : 6,541,508 B2
DATED : April 1, 2003
INVENTOR(S) : Ekwuribe et al.

It is certified that error appears in the above-identified patent and that said Letters Patent is hereby corrected as shown below:

Column 29,
Please replace the structure with

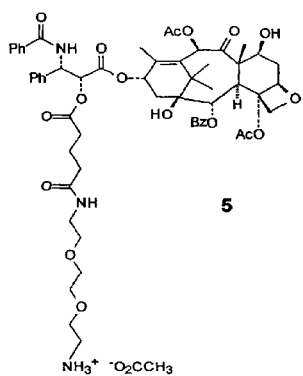

Signed and Sealed this

Seventeenth Day of August, 2004

JON W. DUDAS
*Acting Director of the United States Patent and Trademark Office*